United States Patent
Trayanova et al.

(10) Patent No.: US 10,765,336 B2
(45) Date of Patent: Sep. 8, 2020

(54) SYSTEM AND METHOD FOR PLANNING A PATIENT-SPECIFIC CARDIAC PROCEDURE

(75) Inventors: Natalia A. Trayanova, Baltimore, MD (US); Henry R. Halperin, Baltimore, MD (US); Hermenegild Arevalo, Baltimore, MD (US); Jason Constantino, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 222 days.

(21) Appl. No.: 13/984,741

(22) PCT Filed: Feb. 10, 2012

(86) PCT No.: PCT/US2012/024759
§ 371 (c)(1),
(2), (4) Date: Nov. 20, 2013

(87) PCT Pub. No.: WO2012/109618
PCT Pub. Date: Aug. 16, 2012

(65) Prior Publication Data
US 2014/0088943 A1 Mar. 27, 2014

Related U.S. Application Data

(60) Provisional application No. 61/441,947, filed on Feb. 11, 2011.

(51) Int. Cl.
| | |
|---|---|
| A61B 5/042 | (2006.01) |
| A61B 5/0402 | (2006.01) |
| A61B 6/00 | (2006.01) |
| G06T 19/00 | (2011.01) |
| A61B 34/10 | (2016.01) |
| G16H 50/50 | (2018.01) |
| A61B 8/08 | (2006.01) |
| A61B 5/055 | (2006.01) |
| A61B 6/03 | (2006.01) |
| A61B 8/13 | (2006.01) |
| A61N 1/362 | (2006.01) |

(52) U.S. Cl.
CPC .......... *A61B 5/042* (2013.01); *A61B 5/04021* (2013.01); *A61B 6/503* (2013.01); *A61B 34/10* (2016.02); *G06T 19/00* (2013.01); *G16H 50/50* (2018.01); *A61B 5/055* (2013.01); *A61B 6/032* (2013.01); *A61B 6/037* (2013.01); *A61B 6/466* (2013.01); *A61B 6/5223* (2013.01); *A61B 8/0883* (2013.01); *A61B 8/13* (2013.01); *A61B 2505/05* (2013.01); *A61B 2576/023* (2013.01); *G06T 2210/41* (2013.01)

(58) Field of Classification Search
None
See application file for complete search history.

(56) References Cited

U.S. PATENT DOCUMENTS

| | | |
|---|---|---|
| 5,947,899 A | 9/1999 | Winslow et al. |
| 6,856,830 B2 | 2/2005 | He |
| 2003/0120151 A1* | 6/2003 | Constantinides .... A61K 49/126 |
| | | 600/431 |
| 2005/0018885 A1* | 1/2005 | Chen ....................... G06T 17/00 |
| | | 382/128 |
| 2007/0014452 A1 | 1/2007 | Suresh et al. |
| 2007/0043296 A1 | 2/2007 | Schwartz |
| 2009/0112109 A1 | 4/2009 | Kuklik et al. |
| 2010/0191131 A1* | 7/2010 | Revishvili .......... A61B 5/04011 |
| | | 600/509 |
| 2011/0087088 A1* | 4/2011 | Korn ...................... A61B 5/053 |
| | | 600/411 |
| 2011/0087110 A1* | 4/2011 | Nathan .................. A61B 5/053 |
| | | 600/476 |
| 2012/0002840 A1* | 1/2012 | Linnenbank ............. G06K 9/32 |
| | | 382/103 |

OTHER PUBLICATIONS

Trayanova N. Circ Res. Jan. 7, 2011; 108(1 ): 113-128.*
Toussaint et al. Medical Image Computing and Computer-Assisted Intervention—MICCAI 2010. Lecture Notes in Computer Science vol. 6361, 2010, pp. 418-442.*
Saber et al. Annals of Biomedical Engineering, vol. 29, pp. 275-283, 2001.*
Nieman et al. Magn Reson Med. May 2009; 61(5): 1148-1157.*
Helm et al. Ann. N.Y. Acad. Sci. 1047: 296-307,2005.*
Hsu et al. Heart Circ. Physiol. 43, H1627-H1634, 1998.*
Frangi et al. IEEE Transactions on Medical Imaging, vol. 20, No. 1, 2001, 2-25.*
Adelstein et al., (2007) Scar Burden by Myocardial Perfusion Imaging Predicts Echocardiographic Response to Cardiac Resynchronization Therapy in Ischemic Cardiomyopathy. Am Heart J153, 105-12.
Akar et al., (2007) Dynamic Changes in Conduction Velocity and Gap Junction Properties During Development of Pacing-Induced Heart Failure. Am J Physiol Heart Circ Physiol 293, H1223-30.
Akar et al., (2004) Mechanisms Underlying Conduction Slowing and Arrhythmogenesis in Nonischemic Dilated Cardiomyopathy. Circ Res 95, 717-25.
Aliot et al., EHRA/HRS Expert Consensus on Catheter Ablation of Ventricular Arrhythmias: Developed in a partnership with the European Heart Rhythm Association (EHRA), a Registered Branch of the European Society of Cardiology (ESC), and the Heart Rhythm Society (HRS); in collaboration with the American College of Cardiology (ACC) and the American Heart Association (AHA) Europace. 11, 771- 817 (2009; 2009).

(Continued)

*Primary Examiner* — Michael L Borin
(74) *Attorney, Agent, or Firm* — Venable LLP; Henry J. Daley; Aziz H. Poonawalla

(57) ABSTRACT

A method of planning a patient-specific cardiac procedure according to an embodiment of the current invention includes receiving three-dimensional imaging data of a patient's heart, simulating at least one of electrophysiological or electromechanical activity of at least a portion of the patient's heart using the three-dimensional imaging data, and planning the patient-specific cardiac procedure based on the simulating. The cardiac procedure is for providing a preselected alteration of at least one of electrophysiological or electromechanical behavior of the patient's heart.

34 Claims, 11 Drawing Sheets

(56) References Cited

OTHER PUBLICATIONS

Ansalone et al., (2002) Doppler myocardial imaging to evaluate the effectiveness of pacing sites in patients receiving biventricular pacing. JAm Coll Cardiol 39, 489-99.
Arheden et al., Reperfused rat myocardium subjected to various durations of ischemia: estimation of the distribution volume of contrast material with echo-planar MR imaging *Radiology*. 215, 520-528 (2000).
Ashikaga et al., (2005) Electromechanical analysis of infarct border zone in chronic myocardial infarction. Am J Physiol Heart Circ Physiol 289, H1099-105.
Ashikaga et al., Magnetic resonance-based anatomical analysis of scar-related ventricular tachycardia: implications for catheter ablation *Circ. Res. 101*, 939-947 (2007).
Auricchio et al., (1999) Effect of Pacing Chamber and Atrioventricular Delay on Acute Systolic Function of Paced Patients with Congestive Heart Failure. The Pacing Therapies for Congestive Heart Failure Study Group. The Guidant Congestive Heart Failure Research Group. Circulation 99, 2993-3001.
Auricchio et al., (2003) Clinical Efficacy of Cardiac Resynchronization Therapy Using Left Ventricular Pacing in Heart Failure Patients Stratified by Severity of Ventricular Conduction Delay. JAm Coll Cardiol 42, 2109-16.
Bax et al., (2004) Left Ventricular Dyssynchrony Predicts Response and Prognosis after Cardiac Resynchronization Therapy. J Am Coll Cardiol 44, 1834-40.
Bayer et al., Novel rule based algorithm for assigning myocardial fiber orientation to computation heart models. Ann Biomed Eng. , (in submission) (2012).
Becker et al., (1958) Ventricular excitation; in experimental left bundle branch block. Am Heart J 55, 547-56.
Beg et al., Computational cardiac anatomy using MRI Magn. Reson. Med. 52, 1167-1174 (2004).
Beshai et al., (2007) Cardiac-resynchronization therapy in heart failure with narrow QRS complexes. N Eng J Med 357, 2461-2471.
Bleeker et al., (2006a) Left Ventricular Dyssynchrony in Patients with Heart Failure: Pathophysiology, Diagnosis and Treatment. Nat Clin Pract Cardiovasc Med 3, 213-9.
Bleeker et al., (2006b) Effect of Posterolateral Scar Tissue on Clinical and Echocardiographic Improvement after Cardiac Resynchronization Therapy. Circulation 113, 969-76.
Brugada et al., Nonsurgical transthoracic epicardial radiofrequency ablation: an alternative in incessant ventricular tachycardia. I Am. Coll. Cardiol. 41, 2036-2043 (2003).
Butter et al., (2001) Effect of Resynchronization Therapy Simulation Site on the Systolic Function of Heart Failure Patients. Circulation 104, 3026-9.
Butter et al., (2000) Should Stimulation Site Be Tailored in the Individual Heart Failure Patient? Am J Cardiol 86, 144K-151K.
Callans et al., Efficacy of radiofrequency catheter ablation for ventricular tachycardia in healed myocardial infarction. *Am. J. Cardiol.* 82, 429432 (1998).
Cheng et al., (2008) Heterogeneity of left ventricular wall thickening mechanisms. Circulation 118, 713-721.
Choi et al., (2001) Transmural Extent of Acute Myocardial Infarction Predicts Long-Term Improvement in Contractile Function. Circulation 104, 1101-7.
Chung et al., (2008) Results of the Predictors of Response to CRT (PROSPECT) trial. Circulation 117, 2608-2616.
Cleland et al., (2005) The Effect of Cardiac Resynchronization on Morbidity and Mortality in Heart Failure. N Engl J Med 352, 1539-49.
Clerc, Directional differences of impulse spread in trabecular muscle from mammalian heart. *J. Physiol. (Lond* ). 255, 335-346 (1976).
Constantino et al., (2010) Optimal cardiac; resynchronization therapy is achieved by pacing from the LV region with the longest electromechanical delay. Heart Rhythm 7, S164-165.
Cordeiro et al., (2004) Transmural heterogeneity of calcium activity and mechanical function in the canine left ventricle. Am J Physiol Heart Circ Physiol 286, H1471-9.; [00118].
De Bakker et al., Reentry as a cause of ventricular tachycardia in patients with chronic ischemic heart disease: electrophysiologic and anatomic correlation. *Circulation*. 77, 589-606 (1988).
De Maria et al., Long-Term Outcomes After Cryoablation for Ventricular Tachycardia During Surgical Treatment of Anterior Ventricular Aneurysms *Pacing and Clinical Electrophysiology*. 28, S168-171 (2005).
Delacretaz et al., Catheter ablation of ventricular tachycardia in patients with coronary heart disease: part I: Mapping. Pacing Clin. Electrophysiol. 24, 1261-1277 (2001).
Derval et al., (2010) Optimizing hemodynamics in heart failure patients by systematic screening of left ventricular pacing sites: the lateral left ventricular wall and the coronary sinus are rarely the best sites. JAm Coll Cardiol 55, 566-75.
Dong et al., Impact of heart rhythm status on registration accuracy of the left atrium for catheter ablation of atrial fibrillation../. Cardiovasc. Electrophysiol. 18, 1269-1276 (2007).
Dun et al., Dynamic remodeling of K+ and Ca2+ currents in cells that survived in the epicardial border zone of canine healed infarcted heart. Am. J. Physiol. Heart Circ. Physiol. 287, H1046-54 (2004).
Esther et al., The Critical Isthmus Sites of Ischemic Ventricular Tachycardia are in Zones of Tissue Heterogeneity, Visualized by Magnetic Resonance Imaging Heart Rhythm. (2011).
Fauchier et al., (2002) Interventricular and Intraventricular Dyssynchrony in Idiopathic Dilated Cardiomyopathy: A Prognostic Study with Fourier Phase Analysis of Radionuclide Angioscintigraphy. JAm Coll Cardiol 40, 2022-30.
Fauchier et al., (2003) Reliability of QRS Duration and Morphology on Surface; Electrocardiogram to Identify Ventricular Dyssynchrony in Patients with Idiopathic Dilated Cardiomyopathy. Am J Cardiol 92, 341-4.
Fish et al., (2005) Potential Proarrhythmic; Effects of Biventricular Pacing. J Am Coll Cardiol 46, 2340-7.
Frapier et al., Large encircling cryoablation without mapping for ventricular tachycardia after anterior myocardial infarction: Long-term outcome J. Thorac. Cardiovasc. Surg, 116, 578-583 (1998.
Fung (2009) Effect of left ventricular lead concordance to the delayed contraction segment on echocardiographic and clinical outcomes after cardiac resynchronization therapy. J Cardiovasc Electrophysiol 20, 530-5.
Gima, Y. Rudy, Ionic Current Basis of Electrocardiographic Waveforms: A Model Study. *Circ Res.* 90, 889-896 (2002).
Gurev et al., (2010); Distribution of electromechanical delay in the heart: insights from a three-dimensional electromechanical model. Biophys J 99, 745-54.
Gurev et al., (2011); Models of cardiac electromechanics based on individual hearts imaging data: image-based electromechanical models of the heart. Biomech Model Mechanobiol 10, 295-306.
Helm et al., (2006) Evidence of Structural Remodeling in the Dyssynchronous Failing Heart. Circ Res 98, 125-32.
Helm et al., (2007) Three-Dimensional Mapping of Optimal Left Ventricular Pacing Site for Cardiac Resynchronization. Circulation 115, 953-61.
Hooks et al., (2007) Laminar Arrangement of Ventricular Myocytes Influences Electrical Behavior of the Heart. Circ Res 101, el03-12.
Howard et al., (2011) Improvement in pump function with endocardial biventricular pacing increases with activation time at the left ventricular pacing site in failing canine hearts. Am J Physiol Heart Circ Physiol 301, H1447-55.
Jiang et al., Delayed rectifier K currents have reduced amplitudes and altered kinetics in myocytes from infarcted canine ventricle. *Cardiovasc. Res.* 48, 34-43 (2000).
Kaab et al., (1996) Ionic Mechanism of Action Potential Prolongation in Ventricular Myocytes from Dogs with Pacing-Induced Heart Failure. Circ Res 78, 262-73.
Kass, D. A. (2005) Cardiac Resynchronization Therapy. J Cardiovasc; Electrophysiol 16 Suppl 1, S35-41.

(56) References Cited

OTHER PUBLICATIONS

Khan et al., Effect of radiofrequency catheter ablation of ventricular tachycardia on left ventricular function in patients with prior myocardial infarction J. Interv. Card. Electrophysiol. 7, 243-247 (2002).

Lardo et al., Visualization and temporal/spatial characterization of cardiac radiofrequency ablation lesions using magnetic resonance imaging Circulation. 102, 698-705 (2000).

Larson et al., Analysis of electrically-induced reentrant circuits in a sheet of myocardium. Ann Biomed Eng. 31, 768-80 (2003).

Leclercq et al., (2002) Systolic improvement and mechanical resynchronization does not require electrical synchrony in the dilated failing heart with left bundle-branch block. Circulation 106, 1760-3.

Leclercq et al., (1999) Left Ventricular Lead Insertion Using a Modified Transseptal Catheterization Technique: A Totally Endocardial Approach for Permanent Biventricular Pacing in End-Stage Heart Failure. Pacing Clin Electrophysiol 22, 1570-5.

LeGrice et al., (1995) Transverse Shear Along; Myocardial Cleavage Planes Provides a Mechanism for Normal Systolic Wall Thickening. Circ Res 77, 182-93.

Lindner et al., (2006) Cardiac efficiency and oxygen consumption measured with 11C-acetate PET after long-term cardiac resynchronization therapy. J Nucl Med 47, 378-83.

Lindner et al., (2005) Effect of cardiac resynchronization therapy on global and regional oxygen consumption and myocardial blood flow in patients with non-ischaemic and ischaemic cardiomyopathy. Eur Heart J 26, 70-6.

Lloyd-Jones et al., (2009) Heart Disease and Stroke Statistics—2009 Update: A Report from the American Heart Association Statistics Committee and Stroke Statistics Subcommittee. Circulation 119, 480-6.

Luo, Y. Rudy, A dynamic model of the cardiac ventricular action potential. II. Afterdepolarizations, triggered activity, and potentiation. Circ Res. 74, 1097-1113 (1994).

Marijianowski et al., (1995) Dilated; Cardiomyopathy is Associated with an Increase in the Type I/Type III Collagen Ratio: A Quantitative Assessment. J Am Coll Cardiol 25, 1263-72.

McDowell et al., Susceptibility to arrhythmia in the infarcted heart depends on myofibroblast density *Biophys. J. 101*, 1307-1315 (2011).

Miyazaki et al., (2010) Dyssynchrony indices to predict response to cardiac resynchronization therapy: a comprehensive prospective single-center study. Circ Heart Fail 3, 565-73.

Moreno et al., A computational model to predict the effects of class I anti-arrhythmic drugs on ventricular rhythms *Sci. TransL Med*. 3, 98ra83 (2011).

Nelson et al., (2000) Left Ventricular or Biventricular Pacing Improves Cardiac Function at Diminished Energy Cost in Patients with Dilated Cardiomyopathy and Left Bundle-Branch Block. Circulation 102, 3053-9.

O'Rourke et al., (1999) Mechanisms of Altered Excitation-Contraction Coupling in Canine Tachycardia-Induced Heart Failure, I: Experimental Studies. Circ Res 84, 562-70.

Peters, A. Wit, Myocardial architecture and ventricular arrhythmogenesis. *Circulation*. 97, 1746-1754 (1998).

Pitzalis et al., (2002) Cardiac Resynchronization Therapy Tailored by Echo cardiographic Evaluation of Ventricular Asynchrony. J Am Coll Cardiol 40, 1615-22.

Pu, P. Boyden, Alterations of Na+A+ currents in myocytes from epicardial border zone of the infarcted heart. A possible ionic mechanism for reduced excitability and postrepolarization refractoriness. *Circ. Res*. 81, 110-119 (1997).

Rice et al., (2008) Approximate; model of cooperative activation and crossbridge cycling in cardiac muscle using ordinary differential equations. Biophys J95, 2368-90.

Roes et al., Infarct tissue heterogeneity assessed with contrast-enhanced MRI predicts spontaneous ventricular arrhythmia in patients with ischemic cardiomyopathy and implantable cardioverter-defibrillator Circ. Cardiovasc. Imaging. 2, 183-190 (2009).

Russell et al., (2011) Mechanism of prolonged electromechanical delay in late activated myocardium during left bundle branch block. Am J Physiol Heart Circ Physiol 301, H2334-43.

Sasano et al., Molecular ablation of ventricular tachycardia after myocardial infarction. 12, 1256-1258 (2006).

Schmidt et al., Infarct tissue heterogeneity by magnetic resonance imaging identifies enhanced cardiac arrhythmia susceptibility in patients with left ventricular dysfunction. Circulation. 115, 2006-2014 (2007).

Schuleri et al., Characterization of Peri-Infarct Zone Heterogeneity by Contrast-Enhanced Multidetector Computed Tomography J. Am. Coll. Cardiol. 53, 1699-1707 (2009).

Soejima et al., Catheter ablation in patients with multiple and unstable ventricular tachycardias after myocardial infarction: short ablation lines guided by reentry circuit isthmuses and sinus rhythm mapping. Circulation. 104, 664-669 (2001).

Sosa et al., Nonsurgical transthoracic epicardial catheter ablation to treat recurrent ventricular tachycardia occurring late after myocardial infarction. J. Am. Coll. Cardibl. 35, 1442-1449 (2000).

Spragg et al., (2010) Optimal left ventricular endocardial pacing sites for cardiac resynchronization therapy in patients with ischemic cardiomyopathy. J Am Coll Cardiol 56, 774-81.

St John Sutton et al., (2003) Effect of Cardiac Resynchronization Therapy on Left Ventricular Size and Function in Chronic Heart Failure. Circulation 107, 1985-90.

Suffoletto et al., et al., (2006) Novel speckle-tracking radial strain from routine black-and-white echocardiographic images to quantify dyssynchrony and predict response to cardiac resynchronization therapy. Circulation 113, 960-8.

Suga, H. (1990) Ventricular energetics. Physiol Rev 70, 247-77.

Sutton et al., (2006) Sustained Reverse Left Ventricular Structural Remodeling with Cardiac Resynchronization at One Year is a Function of Etiology: Quantitative Doppler Echo cardiographic Evidence from the Multicenter Insync Randomized Clinical Evaluation (MIRACLE). Circulation 113, 266-72.

Tyberg, J. V., Yeatman, L. A., Parmley, W. W., Urschel, C. W. and; Sonnenblick, E. H. (1970) Effects of hypoxia on mechanics of cardiac contraction. Am J Physiol 218, 1780-8.

Ukkonen et al., (2003) Effect of cardiac resynchronization on myocardial efficiency and regional oxidative metabolism. Circulation 107, 28-31.

Ursell et al., Structural and electrophysiological changes in the epicardial border zone of myocardial infarcts during infarct healing. Circ. Res. 56, 436-452 (1985).

Usyk et al., (2003) Relationship between Regional; Shortening and Asynchronous Electrical Activation in a Three-Dimensional Model of Ventricular Electromechanics. J Cardiovasc Electrophysiol 14, S196-202.

Vadakkumpadan et al., Image-based models of cardiac structure in health and disease Wiley Interdisciplinary Reviews: Systems Biology and Medicine. 2, 489-506 (2010).

Van Deursen et al., (2009) Left ventricular endocardial pacing improves resynchronization therapy in canine left bundle-branch hearts. Circ Arrhythm Electrophysiol 2, 580-7.

Vigmond et al., Computational tools for modeling electrical activity in cardiac tissue. J Electrocardiol. 36, 69-74 (2003).

Walker et al., (2005) MRI-based finite-element analysis of left ventricular aneurysm. Am J Physiol Heart Circ Physiol 289, H692-700.

White et al., (2006) Delayed Enhancement Magnetic Resonance Imaging Predicts Response to Cardiac Resynchronization Therapy in Patients with Intraventricular Dyssynchrony. J Am Coll Cardiol 48, 1953-60.

Wu et al., (2002) Changes in Titin Isoform Expression in Pacing-Induced Cardiac Failure Give Rise to Increased Passive Muscle Stiffness. Circulation 106, 1384-9.

Yan et al., Characterization of the peri-infarct zone by contrast-enhanced cardiac magnetic resonance imaging is a powerful predictor of post-myocardial infarction mortality. Circulation. 114, 32-39 (2006).

Yao et al., Remodeling of gap junctional channel function in epicardial border zone of healing canine infarcts. Circ. Res. 92, 437-443 (2003).

(56) References Cited

OTHER PUBLICATIONS

Yu et al., (2002) Tissue Doppler Echocardiographic Evidence of Reverse Remodeling and Improved Synchronicity by Simultaneously Delaying Regional Contraction after Biventricular Pacing Therapy in Heart Failure. Circulation 105, 438-45.
Zhong et al., On the accuracy of CartoMerge for guiding posterior left atrial ablation in man Heart Rhythm. 4, 595-602 (2007).
International Search Report and Written Opinion of PCT/US2012/024759.
Abdou et al., Quantitative design and evaluation of enhancement/thresholding edge detectors. Proceedings of the IEEE 1979;67(5):753-763.
Adams et al., Seeded region growing. IEEE Transactions on Pattern Analysis & Machine Intelligence 1994;16(6):641-647.
Aguel et al., Advances in Modeling Cardiac Defibrillation. International Journal of Bifurcation and Chaos 2003;13:3791-3805.
Alexander et al., Spatial transformations of diffusion tensor magnetic resonance images. IEEE Transactions on Medical Imaging 2001;20(11):1131-1139.
Aliot et al., EHRA/HRS expert consensus on catheter ablation of ventricular arrhythmias: Developed in a partnership with the European Heart Rhythm Association (EHRA), a registered branch of the European Society of Cardiology (ESC), and the Heart Rhythm Society (HRS); in collaboration with the American College of Cardiology (ACC) and the American Heart Association (AHA). Heart Rhythm 2009;6(6):886-933.
Amado et al., Accurate and objective infarct sizing by contrast-enhanced magnetic resonance imaging in a canine myocardial infarction model. Journal of the American College of Cardiology 2004;44(12):2383-2389.
Anyukhovsky et al., Regional differences in electrophysiological properties of epicardium, midmyocardium, and endocardium. In vitro and in vivo correlations. Circulation 1996;94:1981-1988.
Arevalo et al., Volume of peri-infarct zone determines arrhythmogenesis in infarcted heart. Heart Rhythm 2009;6(5):S232-S333.
Arevalo et al., Arrhythmogenesis in the heart: Multiscale modeling of the effects of defibrillation shocks and the role of electrophysiological heterogeneity. Chaos 2007;17(1):015103.
Arevalo et al., Fiber architecture in infarcted hearts does not significantly affect location of reentry isthmus or optimal ablation site. Heart Rhythm 2010;7:S163.
Ashihara et al., Tunnel Propagation of Postshock Activations as a Hypothesis for Fibrillation Induction and Isoelectric Window. Circ Res 2008;102(6):737-45.
Bayes de Luna et al., Ambulatory sudden cardiac death: mechanisms of production of fatal arrhythmia on the basis of data from 157 cases. American Heart Journal 1989;117(1):151-159.
Beg et al., Computing large deformation metric mappings via geodesic flows of diffeo-morphisms. International Journal of Computer Vision 2005;61(2):139-157.
Bishop et al., The role of photon scattering in optical signal distortion during arrhythmia and defibrillation. Biophysical Journal 2007;93(10):3714-26.
Bruder et al., The influence of inhomogeneous volume conductor models on the ECG and the MCG. Physics in Medicine and Biology 1994;39:1949-1968.
Calkins et al., Catheter ablation of ventricular tachycardia in patients with structural heart disease using cooled radiofrequency energy: Results of a prospective multicenter study. Journal of the American College of Cardiology 2000;35(7):1905-1914.
Camelliti et al., Spatially and temporally distinct expression of fibroblast connexins after sheep ventricular infarction. Cardiovascular Research 2004;62:415-425.
Cappato et al., Worldwide survey on the methods, efficacy, and safety of catheter ablation for human atrial fibrillation. Circulation 2005;111(9);1100-1105.
Cardiac Arrhythmia Suppression Trial (CAST) Investigators. Preliminary report: effect of encainide and flecainide on mortality in a randomized trial of arrhythmia suppression after myocardial infarction. New England Journal of Medicine 1989;321(6):406-412.

Cardinal et al., Anisotropic conduction and functional dissociation of ischemic tissue during reentrant ventricular tachycardia in canine myocardial infarction. Circulation 1988;77:1162-1176.
Ciaccio et al., Model of reentrant ventricular tachycardia based on infarct border zone geometry predicts reentrant circuit features as determined by activation mapping. Heart Rhythm 2007;4(8):1034-1045.
Ciaccio E. Ventricular tachycardia duration and form are associated with electrical discontinuities bounding the core of the reentrant circuit. Journal of Cardiovascular Electrophysiology 2005;16(6):646-654.
Clayton et al., A guide to modelling cardiac electrical activity in anatomically detailed ventricles. Progress in Biophysics and Molecular Biology 2008;96:19-43.
De Bakker et al., Ventricular tachycardia in the infarcted, Langendorff-perfused human heart: role of the arrangement of surviving cardiac fibers. Journal of the American College of Cardiology 1990;15(7):1594-1607.
De Bakker et al., Slow conduction in the infarcted human heart. 'Zigzag' course of activation. Circulation 1993;88(3):915-926.
Drouin et al., Electrophysiologic characteristics of cells spanning the left ventricular wall of human heart: Evidence for presence of M cells. Journal of the American College of Cardiology 1995;26(1):185-192.
Eason et al., The influence of anisotropy on local and global estimates of electrical gradient in computer models of internal defibrillation. Annals of Biomedical Engineering 1998;26:840-849.
Essebag et al., Expanding indications for defibrillators after myocardial infarction: Risk stratifica-tion and cost effectiveness. Cardiac Electrophysiology Review 2004;7(1):43-48.
Estner et al., Abstract 2740: Heterogeneous zones in magnet resonance images are the critical areas for ventricular tachycardia and for successful ablation. Circulation 2009;120(18):S690.
Estner et al., Heterogeneous zones in magnet resonance images are the critical areas for ventricular tachycardia and for successful ablation. Heart Rhythm 2009;6(5):S423.
Estner et al., The critical isthmus sites of ischemic ventricular tachycardia are in zones of tissue heterogeneity, visualized by magnetic resonance imaging, Heart Rhythm 2010.
Faris et al., Novel technique for caridac electromechanical mapping with magnetic resonance imaging tagging and an epicardial electrode sock. Annals of Biomedical Engineering 2003;31;430-440.
Fox et al., Ionic mechanism of electrical alternans. American Journal of Physiology 2002;282:H519-H530.
Grandi et al., A novel computational model of the human ventricular action potential and Ca transient. Journal of Molecular and Cellular Cardiology 2009;48:112-121.
Haralick et al., Image analysis using mathematical morphology. IEEE Transactions on Pattern Analysis & Machine Intelligence 1987;9(4):532-550.
Helm et al., Measuring and mapping cardiac fiber and laminar architecture using diffusion tensor MR imaging. Annals of the New York Academy of Sciences 2005;1047:296-307.
Helm et al., Ex vivo 3D diffusion tensor imaging and quantification of cardiac laminar structure. Magnetic Resonance in Medicine 2005;54(4):850-9.
Herzka et al., An interleaved-navigator projection dual-echo bSSFP sequence for respiratory self-gated imaging. Abstract in Proceedings of the 13th Meeting of the Society for Cardiac Magnetic Resonance 2010;.
Herzka et al., Free breathing cardiac cine imaging with self-gated dual-echo SSFR Abstract in Proceedings of the 17th Meeting of the International Society for Magnetic Resonance in Medicine 2009;.
Jie et al., Mechanisms of mechanically induced spontaneous arrhythmias in acute regional ischemia. Circulation Research 2010;106(1):185-192.
Johnson et al., A computer model for the study of electrical current flow in the human thorax. Computers in Biology and Medicine 1992;22(5):305-323.
Jolley et al., A computer modeling tool for comparing novel ICD electrode orientations in children and adults. Heart Rhythm 2008;5:565-572.

(56) References Cited

OTHER PUBLICATIONS

Josephson et al., Ventricular activation during ventricular endocardial pacing. II Role of pace-mapping to localize origin of ventricular tachycardia. American Journal of Cardiology 1982;50(1)11-22.
Kalman et al., Radiofrequency ablation for cure of atrial flutter. Australian and New Zealand Journal of Medicine 1997;27(6):653-657.
Kavanagh et al., High-current stimuli to the spared epicardium of a large infarct induced ventricular tachycardia. Circulation 1992;85:680-698.
Kellman et al., Phase-sensitive inversion recovery for detecting myocardial infarction using gadolinium-delayed hyperenhancement. Magnetic Resonance in Medicine 2002;47(2):372-383.
Lardo et al., Contrast-enhanced multidetector computed tomography viability imaging after myocardial infarction: Characterization of myocyte death, microvascular obstruction, and chronic scar. Circulation 2006;113:394-404.
Leon et al., Computer model of excitation and recovery in the anisotropic myocardium. I. Rect-angular and cubic arrays of excitable elements. Journal of Electrocardiology 1991;24(1):1-15.
Leon et al., Computer model of excitation and recovery in the anisotropic myocardium. II. Excitation in the simplified left ventricle. Journal of Electrocardiology 1991;24(1)1 7-31.
Li et al., Calcium-activated transient outward chloride current and phase 1 repolarization of swine ventricular action potential. Cardiovascular Research 2003;58(1):89-98.
Li et al., Induction of ventricular arrhythmias following mechanical impact: a simulation study in 3D. Journal of Molecular Histology 2004;35:679-686.
Luo et al., A dynamic model of the ventricular cardiac action potential: I. simulations of ionic currents and concentration changes. Circulation Research 1994;74:1071-1096.
Maleckar et al., Electrotonic coupling between human atrial myocytes and fibroblasts alter myocyte excitability and repolarization. Biophysical Journal 2009;97:2179-2190.
McDowell et al., Fibroblast myocyte coupling causes action potential dispersion in the infarcted heart. Heart Rhythm 2009;6:S295-296.
Moreno et al., Skeletal myoblast implants induce minor propagation delays, but do not promote arrhythmias in the normal swine heart. Europace 2010;Published online Jul. 2010.
Nazarian et al., How to perform magnetic resonance imaging on patients with implantable cardiac arrhythmia devices. Heart Rhythm 2009;6(1):138-143.
Perona et al., Scale-space and edge detection using anisotropic diffusion. IEEE Transactions on Pattern Analysis & Machine Intelligence 1990;12:629-639.
Peters et al., Reduced content of connexin43 gap junctions in ventricular myocardium from hypertrophied and ischemic human hearts. Circulation 1993;88:864-875.
Peters et al., Disturbed connexin43 gap junctional distribution correlates with the location of reentrant circuits in the epicardial border zone of healing canine infarcts that cause ventricular tachycardia. Circulation 1997;95:988-996.
Petersen et al., Lesion dimensions during temperature-controlled radiofrequency catheter ablation of left ventricular porcine myocardium : Impact of ablation site, electrode size, and convective cooling. Circulation 1999;99(2):319-325.
Pierpaoli et al., Toward a quantitative assessment of diffusion anisotropy. Magnetic Resonance in Medicine 1996;36(6):893-906.
Pinto et al., Electrical remodeling in ischemia and infarction. Cardiovascular Research 1999;42:284-297.
Placidi et al., Post-processing noise removal algorithm for magnetic resonance imaging based on edge detection and wavelet analysis. Physics in Medicine and Biology 2003;48(13):1987-1995.
Plank et al., Algebraic multigrid preconditioner for the cardiac bidomain model. IEEE Transactions on Biomedical Engineering 2007;54(4):585-596.
Plank et al., From mitochondria! ion channels to arrhythmias in the heart: Computational techniques to bridge the spatio-temporal scales. Philosophical Transactions A: Mathematical Physical & Engineering Sciences 2008;366(1879):3381-409.
Poelzing et al., Heterogeneous connexin43 expression produces electrophysiological heterogeneities across ventricular wall. American Journal of Physiology 2004;286(5):H2001-2009.
Pollard et al., Computer simulations of three-dimensional propagation in ventricular myocardium. Effects of intramural fiber rotation and inhomogeneous conductivity on epicardial activation. Circulation Research 1993;72(4):744-56.
Prassl et al., Automatically generated, anatomically accurate meshes for cardiac electrophysiology problems. IEEE Transactions on Biomedical Engineering 2009;56(5):1318-30.
Prinzen et al., Mapping of Regional Myocardial Strain and Work During Ventricular Pacing: Experimental Study Using Magnetic Resonance Imaging Tagging. Journal of the American College of Cardiology 1999;33(6):1735-42.
Rodriguez et al., Differences between left and right ventricular chamber geometry affect cardiac vulnerability to electric shocks. Circulation Research 2005;97:168-175.
Romberg et al., Shift-invariant de-noising using wavelet-domain hidden markov trees. IEEE Conference on Signals, Systems, & Computers 1999;.
Roth BJ. Electrical conductivity values with the bidomain model of cardiac tissue. IEEE Transactions on Biomedical Engineering 1997;44:326-328.
Sasano et al., Ventricular tachycardia from the healed myocardial infarction scar: validation of an animal model and utility of gene therapy. Heart Rhythm 2009;6(8):S91-S97.
Schuijf et al., Quantification of myocardial infarct size and transmurality by contrast-enhanced magnetic resonance imaging in men. American Journal of Cardiology 2004;94(3):284-288.
Scollan et al., Histological validation of myocardial microstructure obtained from diffusion tensor magnetic resonance imaging. American Journal of Physiology 1998;275(6):H23082318.
Sengupta et al., Apex-to-Base Dispersion in Regional Timing of Left Ventricular Shortening and Lengthening. Journal of the American College of Cardiology 2006;47(1):163-72.
Stankovicova et al., M cells and transmural heterogeneity of action potential configuration in myocytes from the left ventricular wall of the pig heart. Cardiovascular Research 2000;45(4):952-960.
Stevenson et al., Radiofrequency catheter ablation of ventricular tachycardia after myocardial infarction. Circulation 1998;98(4):308-314.
Stevenson et al., Catheter ablation for ventricular tachycardia. Interventional Cardiac Electrophysiology 2007;115:2750-2760.
Sundar et al., Estimating myocardial fiber orientations by template warping. IEEE International Symposium on Biomedical Imaging 2006;p. 73-76.
Swingen et al., An approach to the three-dimensional display of left ventricular function and viability using MRI. International Journal of Cardiovascular Imaging 2003;19:325326.
Ten Tusscher et al., Alternans and spiral breakup in a human ventricular tissue model. American Journal of Physiology 2006;291(3):H1088-100.
Tice et al., Mechanistic Investigation into the Arrhythmogenic Role of Transmural Heterogeneities in Regional Ischaemia Phase 1 a. Europace 2007;9 Suppl 6:vi46-58.
Trayanova et al., Shock-induced Arrhythmogenesis in the Myocardium. Chaos 2002;359:1327-1337.
Trayanova et al., Computer Simulations of Cardiac Defibrillation: A Look inside the Heart. Computing and Visualization in Science 2002;4:259-270.
Vadakkumpadan et al., Image-based estimation of myoCardial fiber orientations for patient-specific models of cardiac electrophysiology. Heart Rhythm 2009;6(11):1688.
Vadakkumpadan et al., Image-based models of cardiac structure in health and disease. Wiley Interdisciplinary Reviews: Systems Biology and Medicine 2010;2:489-506.
Vadakkumpadan et al., Modeling of whole-heart electrophysiology and mechanics: Towards patient-specific simulations. In: Kerckhoffs Roy, editor. Patient-specific modeling of the cardiovascular system. Springer; 2010. p. 145.

(56) References Cited

OTHER PUBLICATIONS

Vigmond et al., Towards predictive modelling of the electrophysiology of the heart. Experimental Physiology 2009;94(5):563-577.
Weiss et al., Modeling of heterogeneous electrophysiology in the human heart with respect to ECG genesis. Computers in Cardiology 2007;p. 49-52.
Wyman et al., Mapping Propagation of Mechanical Activation in the Paced Heart with MRI Tagging. American Journal of Physiol: Heart and Circulatory Physiology 1999;276(3 Pt 2):H881-91.

* cited by examiner

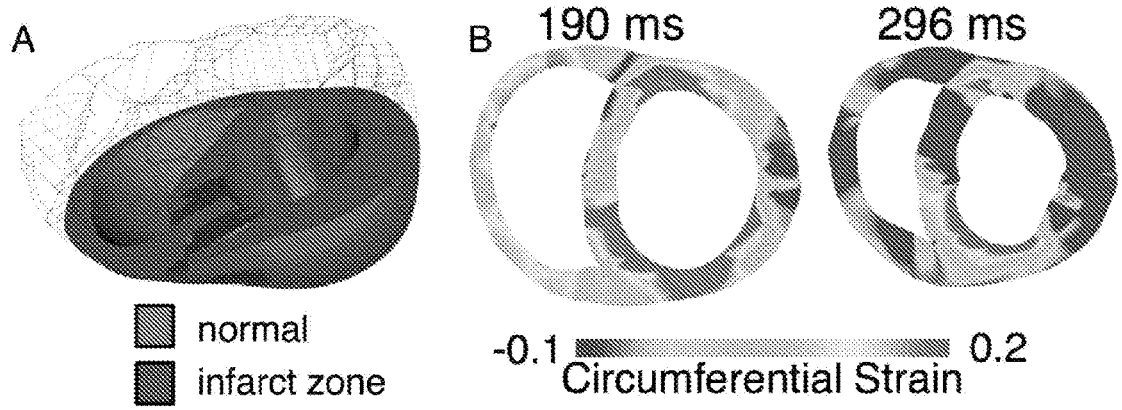
FIG. 10A      FIG. 10B
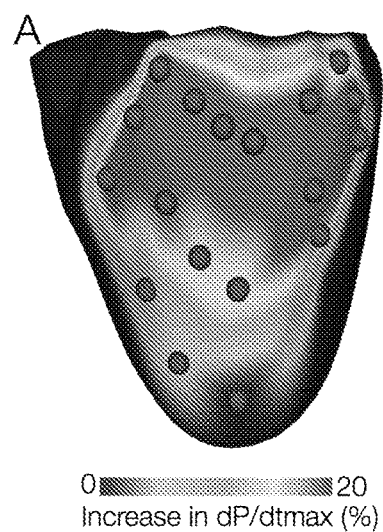 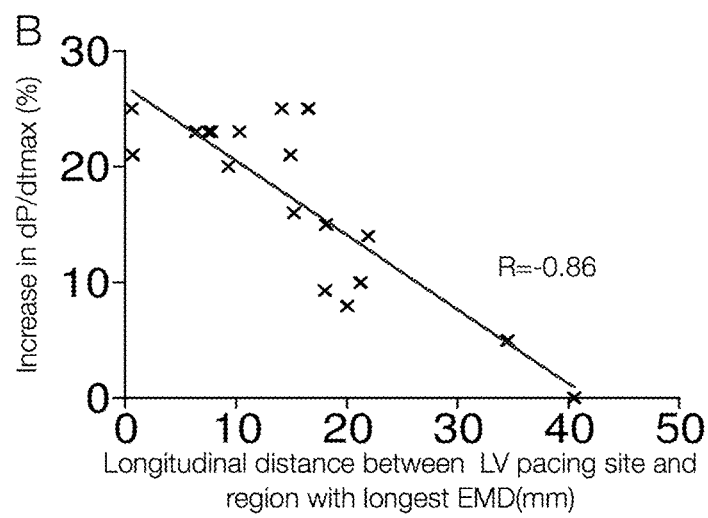
FIG. 11A      Fig. 11B

SYSTEM AND METHOD FOR PLANNING A PATIENT-SPECIFIC CARDIAC PROCEDURE

CROSS-REFERENCE OF RELATED APPLICATION

This is a national stage application under 35 U.S.C. § 371 of PCT/US2012/024759 filed Feb. 10, 2012, the entire contents of which are incorporated herein by reference and that claims priority to U.S. Provisional Application No. 61/441,947, filed Feb. 11, 2011, the entire contents of which are hereby incorporated by reference.

This invention was made with Government support under Grant Nos. HL094610, HL103428, HL099275 and HL103090 awarded by the National Institute of Health (NIH), and Grant No. CBET-0933029, awarded by the National Science Foundation (NSF). The U.S. Government has certain rights in the invention.

BACKGROUND

1. Field of Invention

The field of the currently claimed embodiments of this invention relates to systems and methods for planning patient-specific cardiac procedures.

2. Discussion of Related Art

Ventricular tachyarrhythmia (VT) frequently occurs in the setting of myocardial infarction (MI). Catheter-based ablation is a promising procedure which has become first-line therapy for many types of cardiac arrhythmias (E. Delacretaz, W. G. Stevenson, Catheter ablation of ventricular tachycardia in patients with coronary heart disease: part I: Mapping. *Pacing Clin. Electrophysiol.* 24, 1261-1277 (2001); K. Soejima, M. Suzuki, W. H. Maisel, C. B. Brunckhorst, E. Delacretaz, L. Blier, S. Tung, H. Khan, W. G. Stevenson, Catheter ablation in patients with multiple and unstable ventricular tachycardias after myocardial infarction: short ablation lines guided by reentry circuit isthmuses and sinus rhythm mapping. *Circulation.* 104, 664-669 (2001)). However, catheter ablation has achieved low levels of success in eliminating MI-related VT; only 58% initial success rate and 71% eventual success rate following repeated procedures, with complications rate as high as 8% of the treated population (D. J. Callans, E. Zado, B. H. Sarter, D. Schwartzman, C. D. Gottlieb, F. E. Marchlinski, Efficacy of radiofrequency catheter ablation for ventricular tachycardia in healed myocardial infarction. *Am. J. Cardiol.* 82, 429-432 (1998)).

The low efficacy of catheter ablation for infarct-related VT stems from the fact that current voltage and pace mapping techniques to identify the targets of ablation are associated with numerous limitations, including ambiguities in correlating maps with anatomy (J. Dong, D. Dalal, D. Scherr, A. Cheema, S. Nazarian, K. Bilchick, I. Almasry, A. Cheng, C. A. Henrikson, D. Spragg, J. E. Marine, R. D. Berger, H. Calkins, Impact of heart rhythm status on registration accuracy of the left atrium for catheter ablation of atrial fibrillation. *J. Cardiovasc. Electrophysiol.* 18, 1269-1276 (2007)), and insufficient resolution in identifying ablation targets, resulting from the point-by-point sampling nature of current mapping techniques (J. Brugada, A. Berruezo, A. Cuesta, J. Osca, E. Chueca, X. Fosch, L. Wayar, L. Mont, Nonsurgical transthoracic epicardial radiofrequency ablation: an alternative in incessant ventricular tachycardia. *J. Am. Coll. Cardiol.* 41, 2036-2043 (2003); E. Sosa, M. Scanavacca, A. d'Avila, F. Oliveira, J. A. Ramires, Nonsurgical transthoracic epicardial catheter ablation to treat recurrent ventricular tachycardia occurring late after myocardial infarction. *J. Am. Coll. Cardiol.* 35, 1442-1449 (2000); H. Zhong, J. M. Lacomis, D. Schwartzman, On the accuracy of CartoMerge for guiding posterior left atrial ablation in man *Heart Rhythm.* 4, 595-602 (2007)). Furthermore, the complex 3D pathways along which the cardiac impulse propagates around/through the zone of infarct during VT, are difficult to reconstruct on the basis of electrical interrogation of ventricular surfaces only (J. M. de Bakker, F. J. van Capelle, M. J. Janse, A. A. Wilde, R. Coronel, A. E. Becker, K. P. Dingemans, N. M. van Hemel, R. N. Hauer, Reentry as a cause of ventricular tachycardia in patients with chronic ischemic heart disease: electrophysiologic and anatomic correlation. *Circulation.* 77, 589-606 (1988); N. Peters, A. Wit, Myocardial architecture and ventricular arrhythmogenesis. *Circulation.* 97, 1746-1754 (1998)). These limitations prolong procedure duration, greatly increasing the risk of chamber perforation, thromboemboli, and radiation overexposure, and limit the success of the therapy.

New approaches that deliver swift and accurate identification of optimal infarct-related VT ablation targets will dramatically improve the efficacy of the therapy and increase its tolerance while reducing post-procedure complications. This will result in a dramatic medical and economic impact on both the lives of patients and the society at large.

In addition, heart failure is a major cause of morbidity and mortality, contributing significantly to global health expenditure. Heart failure patients often exhibit contractile dyssynchrony, which diminishes cardiac systolic function. Cardiac resynchronization therapy (CRT), a treatment modality that employs bi-ventricular (bi-V) pacing to re-coordinate the contraction of the heart, is a valuable therapeutic option for such patients. CRT has been shown to improve heart failure symptoms and reduce hospitalization, yet approximately 30% of patients fail to respond to the therapy. The poor predictive ability of current approaches to identify potential responders to CRT reflects the incomplete understanding of the complex pathophysiologic and electromechanical factors that need to be considered to achieve optimal resynchronization in each dyssynchronous heart.

Therefore, there remains a need for improved systems and methods for planning patient-specific cardiac procedures.

SUMMARY

A method of planning a patient-specific cardiac procedure according to an embodiment of the current invention includes receiving three-dimensional imaging data of a patient's heart, simulating at least one of electrophysiological or electromechanical activity of at least a portion of the patient's heart using the three-dimensional imaging data, and planning the patient-specific cardiac procedure based on the simulating. The cardiac procedure is for providing a preselected alteration of at least one of electrophysiological or electromechanical behavior of the patient's heart.

A computer-readable medium according to an embodiment of the current invention includes computer-executable code for planning a patient-specific cardiac procedure, the computer-executable code includes instructions that, when executed by the computer, causes the computer to receive three-dimensional imaging data of a patient's heart, simulate at least one of electrophysiological or electromechanical activity of at least a portion of the patient's heart using the three-dimensional imaging data, and provide simulation results for planning the patient-specific cardiac procedure. The cardiac procedure is for providing a preselected alteration of at least one of electrophysiological or electromechanical behavior of the patient's heart.

A system for planning a patient-specific cardiac procedure according to an embodiment of the current invention includes a data processor configured with computer-executable code, the computer-executable code comprising instructions that, when executed by the data processor, causes the data processor to receive magnetic resonance three-dimensional imaging data of a patient's heart, simulate at least one of electrophysiological or electromechanical activity of at least a portion of the patient's heart using the three-dimensional imaging data, and provide simulation results for planning the patient-specific cardiac procedure. The cardiac procedure is for providing a preselected alteration of at least one of electrophysiological or electromechanical behavior of the patient's heart.

BRIEF DESCRIPTION OF THE DRAWINGS

Further objectives and advantages will become apparent from a consideration of the description, drawings, and examples.

FIG. 10A shows a computational mesh for the mechanical component of the MRI-based electromechanical model of post-MI canine heart according to an embodiment of the current invention. The infarct zone (scar with peri-infarct) is demarcated in blue. FIG. 10B shows transmural distribution of fiber strain during sinus rhythm at two instants of time. Reference state is the unloaded state.

FIG. 11A provides a map of the percentage increase in $dP/dt_{max}$ as a function of the LV pacing site. Red dots denote LV pacing sites. FIG. 11B provides correlation of longitudinal distance between LV pacing site and region with longest EMD, and percentage increase in $dP/dt_{max}$.

DETAILED DESCRIPTION

Figures 1A, 1B, 1C, 1D, 1E, 1F, 1G:
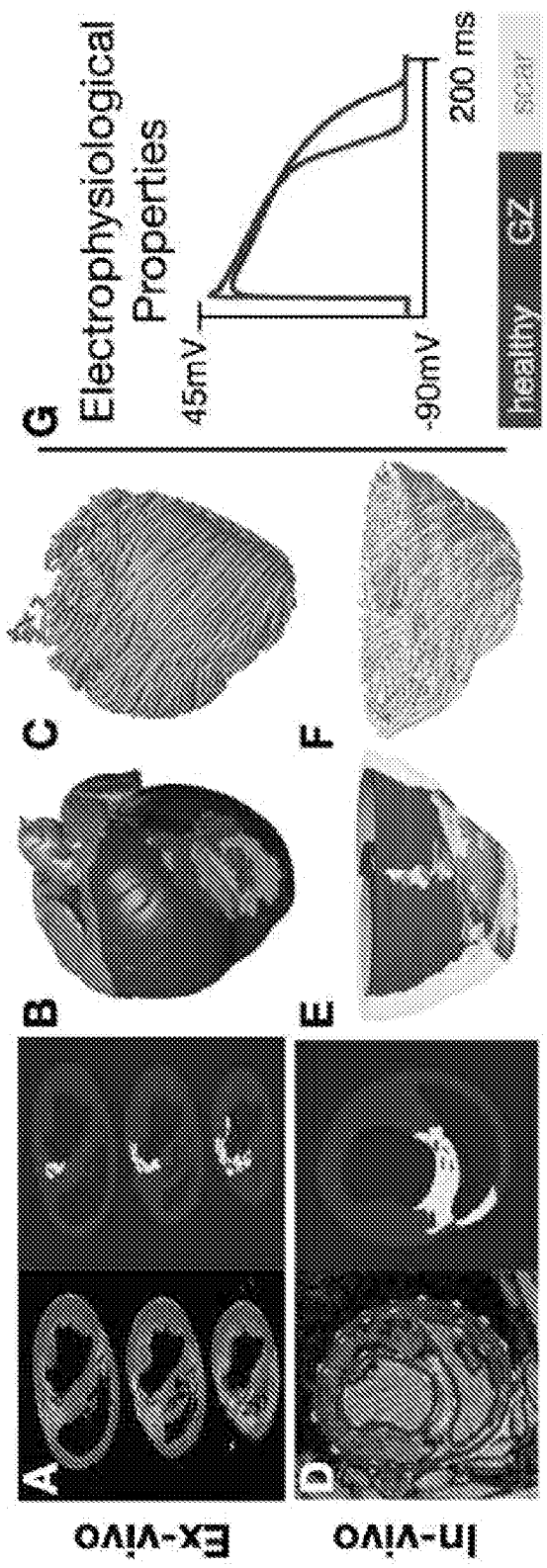
FIGS. 1A-1G show the model creation pipeline according to an embodiment of the current invention. A. Ex-vivo MRIs of an infarcted canine heart with corresponding segmentation. B. 3D model with epicardium rendered semi-transparent. C. Streamline representation of fibers obtained from DTMRI. D. In-vivo MRI of infarcted pig heart with corresponding segmentation. E. Model with epicardium rendered semi-transparent. F. Streamlines of approximated fibers. G. Action potentials of healthy myocytes and GZ cells.

Some embodiments of the current invention are discussed in detail below. In describing embodiments, specific terminology is employed for the sake of clarity. However, the invention is not intended to be limited to the specific terminology so selected. A person skilled in the relevant art will recognize that other equivalent components can be employed and other methods developed without departing from the broad concepts of the current invention. All references cited anywhere in this specification, including the Background and Detailed Description sections, are incorporated by reference as if each had been individually incorporated.

According to some embodiments of the current invention, we introduce a novel multiscale electrophysiological modeling methodology, which we term "virtual electrophysiology (EP) lab," which we apply to the prediction of the optimal targets of catheter ablation of infarct-related monomorphic ventricular tachycardia (VT) in individual hearts. Determining what constitutes an optimal target of VT ablation is based on a novel mechanistic understanding of the organization of VT in myocardial infarction (MI) obtained in the present study. Predicting where these optimal ablation targets are located in an individual heart with its specific infarct morphology is based on MRI-based multiscale computational modeling of electrophysiology in that heart according to some embodiments of the current invention. We take advantage of advanced image-processing and computational-anatomy tools (H. Ashikaga, T. Sasano, J. Dong, M. M. Zviman, R. Evers, B. Hopenfeld, V. Castro, R. H. Helm, T. Dickfeld, S. Nazarian, J. K. Donahue, R. D. Berger, H. Calkins, M. R. Abraham, E. Marban, A. C. Lardo, E. R. McVeigh, H. R. Halperin, Magnetic resonance-based anatomical analysis of scar-related ventricular tachycardia: implications for catheter ablation Circ. Res. 101, 939-947 (2007); M. F. Beg, P. A. Helm, E. McVeigh, M. I. Miller, R. L. Winslow, Computational cardiac anatomy using MRI Magn. Reson. Med. 52, 1167-1174 (2004)), a high-throughput pipeline for MRI-based individualized heart model generation (F. Vadakkumpadan, H. Arevalo, A. J. Prassl, J. Chen, F. Kickinger, P. Kohl, G. Plank, N. Trayanova, Image-based models of cardiac structure in health and disease Wiley Interdisciplinary Reviews: Systems Biology and Medicine. 2, 489-506 (2010)), and sophisticated numerical simulation and analysis approaches (E. Vigmond, M. Hughes, G. Plank, L. J. Leon, Computational tools for modeling electrical activity in cardiac tissue. J. Electrocardiol. 36, 69-74 (2003)) to evaluate the VT circuits associated with the individual infarct morphology and to predict the optimal targets of VT ablation in the given heart. This approach paves the way for a major paradigm shift in the clinical procedure of VT ablation, where identification of the optimal ablation targets in each individual heart would be carried out non-invasively by the present simulation methodology prior to the clinical procedure. Delivery of catheter ablation will then be minimally-invasive, swift and precise, eradicating all infarct-related VTs.

We first present a new mechanistic understanding of VT maintenance in infarcted hearts and how this new understanding allows for the accurate prediction, by means of computational modeling of arrhythmia in the individual heart, of the optimal targets of VT ablation. We then provide examples of the success of this "virtual EP lab" approach in accurately identifying the optimal ablation targets in a retrospective animal study.

Computational Modeling of Electrophysiology in Individual Ex-Vivo and In-Vivo Infarcted Hearts Ex-Vivo Heart Models.

To understand the mechanisms maintaining VT in MI and how that knowledge can be used to determine the optimal targets of infarct-related VT ablation, we used a biophysically-detailed model of an individual canine heart with MI reconstructed from high-resolution ex-vivo MRI and diffusion tensor (DT)-MRI scans. FIGS. 1A-1C present the generation of the geometrical and structural aspects of the canine heart model. Infarcted tissue in the ventricles is discriminated from the rest of the myocardium, with the infarct further segmented out (FIG. 1A) into infarct scar and remodeled myocardium, the latter often referred to as border, peri-infarct, or gray zone (A. Schmidt, C. F. Azevedo, A. Cheng, S. N. Gupta, D. A. Bluemke, T. K. Foo, G. Gerstenblith, R. G. Weiss, E. Marban, G. F. Tomaselli, J. A. Lima, K. C. Wu, Infarct tissue heterogeneity by magnetic resonance imaging identifies enhanced cardiac arrhythmia susceptibility in patients with left ventricular dysfunction. Circulation. 115, 2006-2014 (2007)) based on the appearance of remodeled tissue in clinical MR images. Below we use the term gray zone (GZ). The resulting infarct segmentation shows strands of GZ tissue interdigitated with the electrically inert scar tissue, forming numerous channels within the scar. Separation of the atria from the ventricles completes the geometric reconstruction of the model (FIG. 1B). Fiber orientation is based on DT-MRI data (FIG. 1C). A similar approach for ex-vivo MRI-based heart reconstruction has been used in our recent studies (J. D. Moreno, Z. I. Zhu, P. C. Yang, J. R. Bankston, M. T. Jeng, C. Kang, L. Wang, J. D. Bayer, D. J. Christini, N. A. Trayanova, C. M. Ripplinger, R. S. Kass, C. E. Clancy, A computational model to predict the effects of class I anti-arrhythmic drugs on ventricular rhythms Sci. Transl. Med 3, 98ra83 (2011); K. S. McDowell, H. J. Arevalo, M. M. Maleckar, N. A. Trayanova, Susceptibility to arrhythmia in the infarcted heart depends on myofibroblast density Biophys. J. 101, 1307-1315 (2011); V. Gurev, T. Lee, J. Constantino, H. Arevalo, N. A. Trayanova, Models of cardiac electromechanics based on individual hearts imaging data: image-based electromechanical models of the heart Biomech. Model. Mechanobiol. 10, 295-306 (2011)).

The canine heart is characterized with an extensive GZ (P. Ursell, P. Gardner, A. Albala, J. F. Jr., A. Wit, Structural and electrophysiological changes in the epicardial border zone of myocardial infarcts during infarct healing. Circ. Res. 56, 436-452 (1985)), while infarcted swine (the animal model used to demonstrate the capabilities of our approach, see below) and human hearts have been shown to be arrhythmogenic with smaller GZs. To create cardiac geometrical models with the same infarct scar but with different (smaller) GZ volumes, the GZ was "morphologically eroded," decreasing GZ volume while preserving object topology.

In-Vivo Heart Models.

To demonstrate that our simulation methodology can successfully predict the optimal ablation targets, we conducted a retrospective modeling study of infarct-related VT ablation in swine hearts. Models were generated from in-vivo MRI scans pre-ablation (FIG. 1D). To the best of our knowledge, this is the first development and application of heart models from in-vivo MRI. While the general electrophysiological model generation pipeline was similar to that for ex-vivo hearts, there were also significant differences. The first was in the segmentation process (FIG. 1D), where the ventricles were segmented by fitting cubic splines around manually identified landmark points demarcating the epicardial and endocardial surfaces; the full in-vivo geometrical model is shown in FIG. 1E. The second difference consisted in the fact that fiber orientation could not be acquired in this case. Therefore, fiber orientation was assigned in the in-vivo reconstructed hearts (FIG. 1F) using a novel geometry-driven approach (J. D. Bayer, R. Blake, G. Plank, Trayanova N, Novel rule based algorithm for assigning myocardial fiber orientation to computation heart models. Ann Biomed Eng., (in submission) (2012)).

Assigning Electrophysiological Properties.

The ex-vivo and in-vivo electrophysiological ventricular models were completed by assigning different electrophysiological properties to normal and GZ tissue; biophysically-detailed models of the action potentials (see Methods, below) in these regions are shown in FIG. 1G. Scar and ablation lesions were assumed electrically insulating.

The 3D Organizing Centers of Infarct-Related Monomorphic VT are Contained within the Infarct GZ Using the canine ex-vivo model (GZ volume=5.0 cm$^3$), we simulated programmed electrical stimulation (PES) delivered from 27 different endocardial sites. The PES protocol consisted of pacing at a cycle length of 300 ms for 6 beats followed by one or two premature extrastimuli delivered at shorter intervals until VT was induced, similar to protocols used in experimental studies (H. Ashikaga, T. Sasano, J. Dong, M. M. Zviman, R. Evers, B. Hopenfeld, V. Castro, R. H. Helm, T. Dickfeld, S. Nazarian, J. K. Donahue, R. D. Berger, H. Calkins, M. R. Abraham, E. Marban, A. C. Lardo, E. R. McVeigh, H. R. Halperin, Magnetic resonance-based anatomical analysis of scar-related ventricular tachycardia: implications for catheter ablation *Circ. Res.* 101, 939-947 (2007); T. Sasano, A. D. McDonald, K. Kikuchi, J. K. Donahue, Molecular ablation of ventricular tachycardia after myocardial infarction. 12, 1256-1258 (2006)). Monomorphic VT was induced in the model following PES from 8 out of the 27 pacing sites. VT persisted for the entire 2 s of simulated time interval. Pseudo-ECGs were calculated in all cases, as described in Methods.

Figures 2A, 2B, 2C:
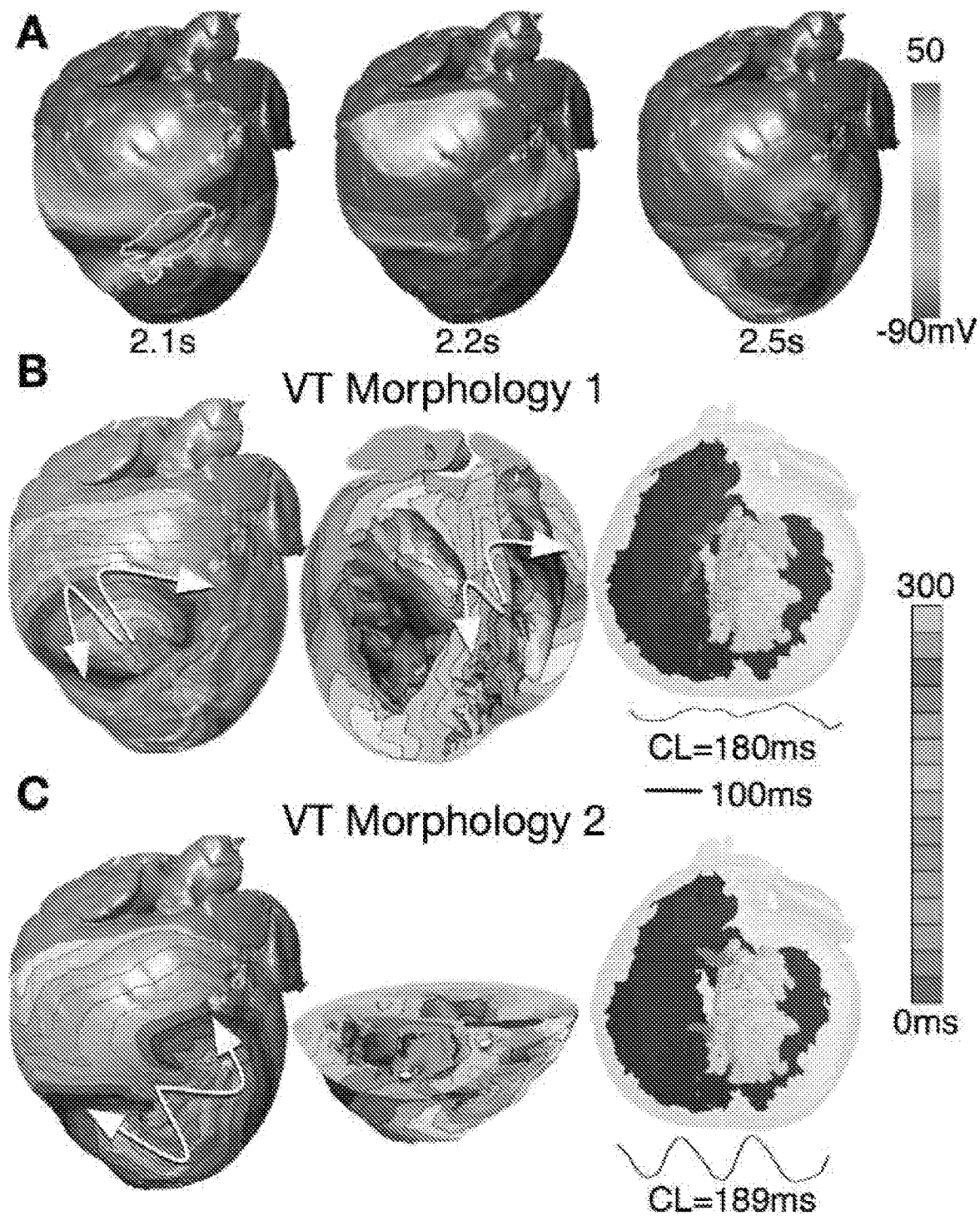
FIGS. 2A-2C show VT induction in the canine heart. A. Transmembrane potential maps during PES (GZ outlined in white). B. Activation map, VT morphology 1, demonstrating figure-of-eight reentry on the epicardium and RV endocardium. Reentry circuits are organized around two I-type filaments (pink lines) located within GZ with endpoints on the epicardium and RV endocardium. C. VT morphology 2, manifested as figure-of-eight reentry on epicardium and breakthroughs on endocardium (white dots). Reentry was organized around two I-type filaments with endpoints on the epicardium and scar.

For all VTs induced, reentry initiation took place within the GZ. FIG. 2A presents transmembrane potential maps depicting the events leading to reentry initiation for PES from the LV apex. The GZ exhibited slowed conduction and longer recovery time compared to the surrounding healthy tissue (FIG. 2A, 2.1 s). This resulted in conduction block (FIG. 2A, 2.2 s), wavebreak, and reentry formation (FIG. 2A, 2.5 s). For all PES sites resulting in VT induction, the reentrant circuit was manifested as a figure-of-eight pattern on the epicardium.

VT morphologies induced from the eight pacing sites were not all unique. Comparison of pseudo-ECGs demonstrated two distinct VT morphologies. The first VT morphology resulted from PES at two sites, both on RV, and had an average cycle length of 190 ms. The reentrant circuit was a figure-of-eight pattern on the epicardium and RV endocardium (FIG. 2B). To gain further insight into the spatiotemporal organization of the VT circuit, the organizing centers of reentry (the filaments) were calculated (see Methods). For this VT morphology, the reentry revolved around two I-type filaments with endpoints at the epicardium and RV endocardium (FIG. 2B, pink lines). The filaments were fully contained within the GZ and the endpoints remained in the same locations for the duration of the VT.

The second VT morphology resulted from PES at six LV endocardial sites. The average cycle length, 222±17 ms, was longer than that of the first VT morphology. The figure-of-eight reentry on the epicardium had chirality opposite to that of the first VT morphology, and was manifested as breakthroughs on LV and RV endocardial surfaces (FIG. 2C). This was due to the reentrant activity being organized around two I-type filaments with endpoints at the epicardium and the infarct scar. Since the filaments did not extend to the endocardium, no rotational activity was observed there. Both filaments were stably located within the GZ throughout the VT duration.

Figures 3A, 3B, 3C:
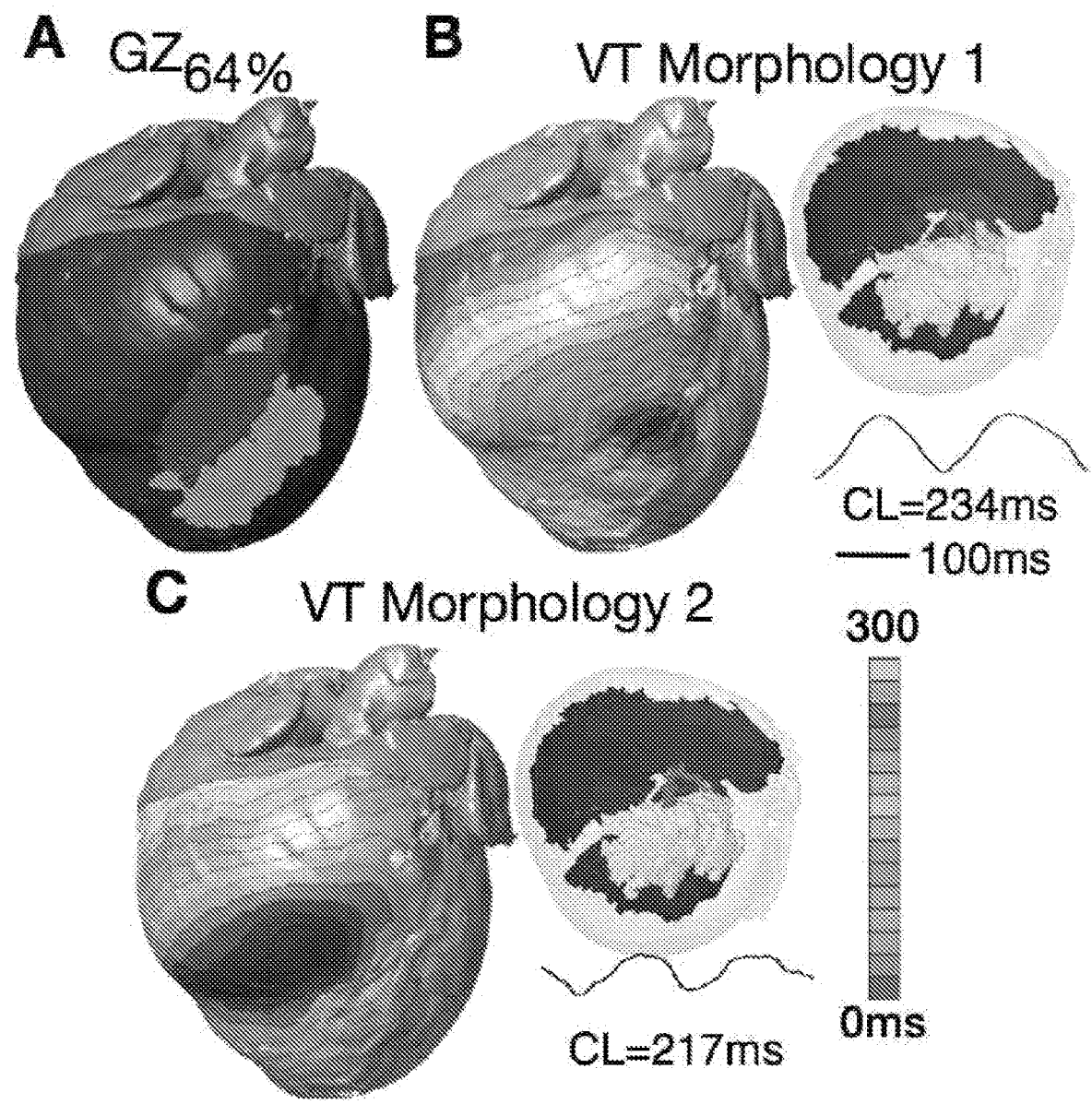
FIGS. 3A-3C show morphological erosion of GZ. A. Model with GZ volume 64% of the original. B. and C. Activation maps of the two VT morphologies induced after PES; both manifest as breakthrough on the epicardium and are organized around a U-type filament with endpoints on the scar.

Decreasing GZ volume by morphological erosion to values found in arrhythmogenic swine (K. H. Schuleri, M. Centola, R. T. George, L. C. Amado, K. S. Evers, K. Kitagawa, A. L. Vavere, R. Evers, J. M. Hare, C. Cox, E. R. McVeigh, J. A. C. Lima, A. C. Lardo, Characterization of Peri-Infarct Zone Heterogeneity by Contrast-Enhanced Multidetector Computed Tomography *J. Am. Coll. Cardiol.* 53, 1699 <last_page> 1707 (2009)) or human hearts (A. Schmidt, C. F. Azevedo, A. Cheng, S. N. Gupta, D. A. Bluemke, T. K. Foo, G. Gerstenblith, R. G. Weiss, E. Marban, G. F. Tomaselli, J. A. Lima, K. C. Wu, Infarct tissue heterogeneity by magnetic resonance imaging identifies enhanced cardiac arrhythmia susceptibility in patients with left ventricular dysfunction. *Circulation.* 115, 2006-2014 (2007)) with MI resulted in the GZ becoming intramural and no longer extending to the epicardium as in the canine ventricles. In the model with GZ at 64% of the original volume (FIG. 3A, GZ=3.23 cm$^3$), PES from the same 27 endocardial sites induced 9 VTs (average cycle length 227±23 ms) with two distinct pseudo-ECG morphologies (FIGS. 3B-3C). For both VT morphologies, the VT manifested itself as a breakthrough on both endo- and epicardium (FIGS. 3B-3C), with a figure-of-eight intramural pattern. The reentrant activity was organized around a single U-type filament attached with both ends to the scar and fully contained within the GZ.

Further reduction of GZ to 37% of the original volume (1.88 cm$^3$) resulted in VT induction by PES from 7 sites with an average VT cycle length of 196±7 ms; all VTs had the same morphology. VT was similarly organized around a U-type filament located in its entirety within GZ, which remained stable for the duration of the simulation. Reentry was again intramural with breakthroughs on both epi- and endocardial surfaces.

Decreasing GZ Below Critical Size Results in VT Non-Inducibility

Further morphological erosion of GZ resulting in the critical GZ volume of 12.6% of the original (0.76 cm$^3$) resulted in inability to induce VT from any pacing site. In this case, the GZ volume was too small to support filament formation. No VT could be induced for any GZ volume below this critical value. These results indicate that there is a minimum GZ volume necessary to support filament formation in this heart.

The critical GZ volume obtained in our simulations is comparable to that reported in experiments. Using in-vivo MRI with late gadolinium enhancement (LGE) of pig hearts with MI, Estner et al (H. L. Estner, M. M. Zviman, D. Herzka, F. Miller, V. Castro, S. Nazarian, H. Ashikaga, Y. Dori, R. D. Berger, H. Calkins, A. C. Lardo, H. R. Halperin, The Critical Isthmus Sites of Ischemic Ventricular Tachycardia are in Zones of Tissue Heterogeneity, Visualized by Magnetic Resonance Imaging *Heart Rhythm.* (2011)) found that hearts with non-inducible VT had GZ volumes 13±5% of total infarct volume. These findings match ours: in the model where GZ volume was reduced to 12.6% of total infarct volume (the critical value of 0.76 cm,$^3$ as described above), VT was not inducible. Our simulations demonstrate that large GZ volumes were able to support a larger number of stable filaments, resulting in multiple VT morphologies arising from the same infarct geometry (FIGS. 2-3). Intermediate GZ volumes were able to support typically a single filament giving rise to the same VT morphology regardless of PES site, while GZ volumes below the critical value resulted in VT non-inducibility due to insufficient amount of electrically remodeled tissue to support reentrant activity.

Targeting of Filaments in the GZ for Optimal VT Ablation

The results presented above suggest that targeting GZ with catheter ablation to decrease its size and bring it below the critical volume for sustaining reentrant activity would result in successful termination of VT. This approach has recently been validated in a retrospective study that showed that successful ablation sites, as determined during standard electrophysiological study, co-localized with GZ (H. L.

Estner, M. M. Zviman, D. Herzka, F. Miller, V. Castro, S. Nazarian, H. Ashikaga, Y. Dori, R. D. Berger, H. Calkins, A. C. Lardo, H. R. Halperin, The Critical Isthmus Sites of Ischemic Ventricular Tachycardia are in Zones of Tissue Heterogeneity, Visualized by Magnetic Resonance Imaging *Heart Rhythm*. (2011)). Results from recent clinical ablations studies have demonstrated a significant benefit from encircling the infarct scar with ablation lesions (J. M. Frapier, J. J. Hubaut, J. L. Pasquie, P. A. Chaptal, Large encircling cryoablation without mapping for ventricular tachycardia after anterior myocardial infarction: Long-term outcome *J. Thorac. Cardiovasc. Surg.* 116, 578 <last_page> 583 (1998); R. G. De Maria, M. Mukaddirov, P. Rouviere, E. Barbotte, B. Celton, B. Albat, J. Frapier, Long-Term Outcomes After Cryoablation for Ventricular Tachycardia During Surgical Treatment of Anterior Ventricular Aneurysms *Pacing and Clinical Electrophysiology*. 28, S168-171 (2005)). However, such an approach results in increased damage to functioning myocardium that could lead to depressed ventricular function (K. Soejima, M. Suzuki, W. H. Maisel, C. B. Brunckhorst, E. Delacretaz, L. Blier, S. Tung, H. Khan, W. G. Stevenson, Catheter ablation in patients with multiple and unstable ventricular tachycardias after myocardial infarction: short ablation lines guided by reentry circuit isthmuses and sinus rhythm mapping. *Circulation*. 104, 664-669 (2001); H. H. Khan, W. H. Maisel, C. Ho, M. Suzuki, K. Soejima, S. Solomon, W. G. Stevenson, Effect of radiofrequency catheter ablation of ventricular tachycardia on left ventricular function in patients with prior myocardial infarction *J. Interv. Card. Electrophysiol.* 7, 243-247 (2002)); current clinical guidelines encourage targeted approaches that minimize the ablation lesion (E. M. Aliot, W. G. Stevenson, J. M. Almendral-Garrote, F. Bogun, C. H. Calkins, E. Delacretaz, P. D. Bella, G. Hindricks, P. Jais, M. E. Josephson, J. Kautzner, G. N. Kay, K.-. Kuck, B. B. Lerman, F. Marchlinski, V. Reddy, M.-. Schalij, R. Schilling, K. Soejima, D. Wilber, EHRA/HRS Expert Consensus on Catheter Ablation of Ventricular Arrhythmias: Developed in a partnership with the European Heart Rhythm Association (EHRA), a Registered Branch of the European Society of Cardiology (ESC), and the Heart Rhythm Society (HRS); in collaboration with the American College of Cardiology (ACC) and the American Heart Association (AHA) *Europace*. 11, 771 <last_page> 817 (2009; 2009)).

Based on the new mechanistic insight regarding VT maintenance in the zone of infarct, and specifically, the fact that the scroll-wave filaments were anchored in specific regions of the GZ while being fully contained within the GZ, as described above, we hypothesized that ablating GZ region(s) containing the scroll wave filament(s) would terminate all VTs. To test this hypothesis, ablation lesions that encompass the scroll-wave filaments were implemented in all models with different GZ volumes; the lesions were assumed electrically inactive.

Figures 4A, 4B:
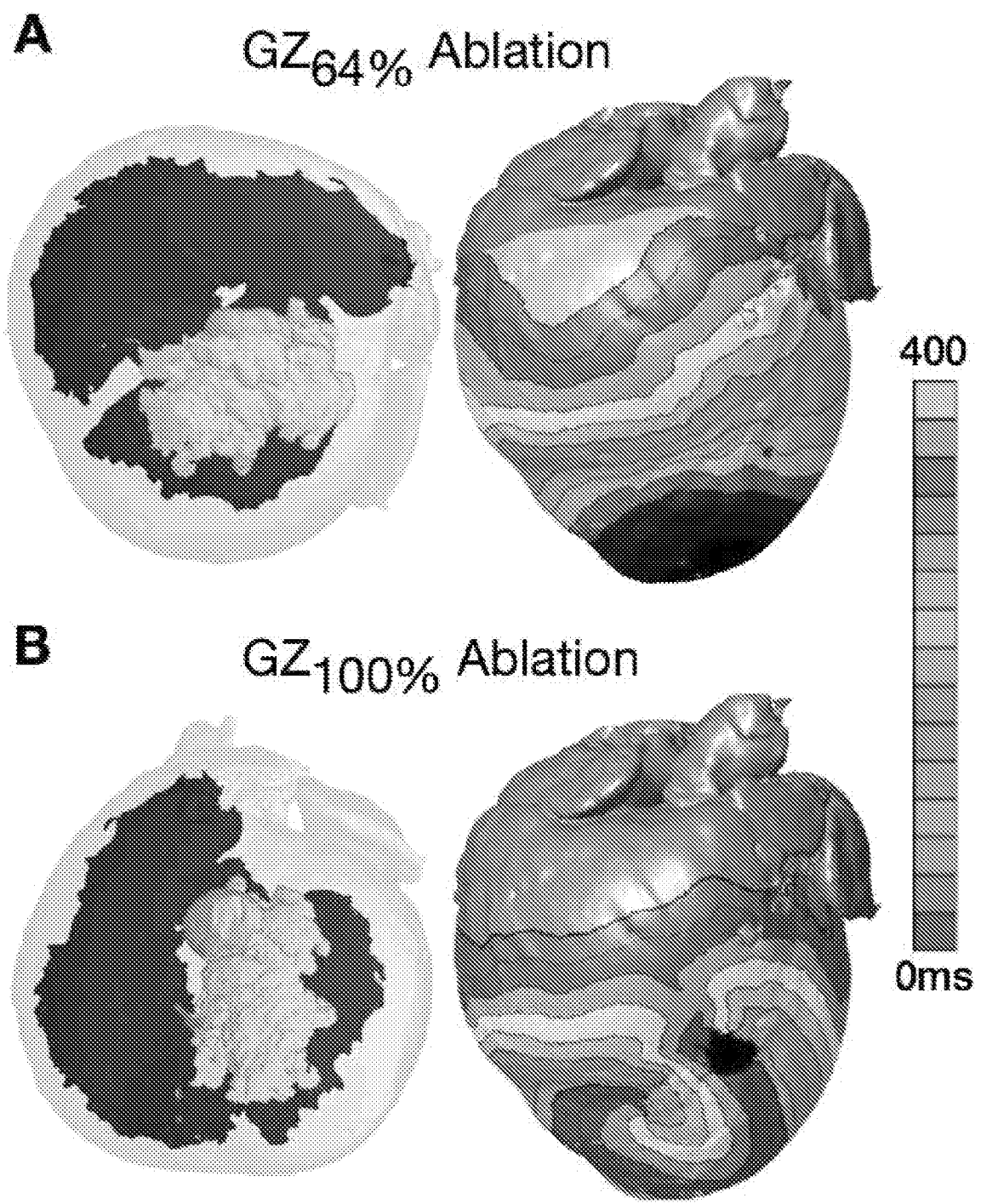
FIGS. 4A and 4B show targeting filaments for ablation. A. Ablating the site of U-type filament formation shown in FIG. 3B-3C results in VT non-inducibility. B. Ablating only one of I-type filaments shown in FIG. 2C results in ablation failure. The resulting reentry is organized around a different I-type filament with endpoints on epicardium and scar.

FIG. 4A presents ablation of the tissue in which the U-shaped scroll-wave filament sustaining each of the VTs shown in FIGS. 3B-3C was formed. Model ablation was successful and VT could no longer be induced by PES from any of the 27 sites (FIG. 4A). Similar was the outcome of ablation in the other models (different GZ volume) where VT was sustained by a single U-shaped filament (not shown here). Importantly, while the ablation in FIG. 4A decreased GZ volume (to 2.84 cm$^3$), it did not bring it below the critical level for which VT can no longer be initiated (0.76 cm$^3$). Thus, targeting the scroll-wave filaments sustaining VT, all of which are contained within GZ, is the most effective way of terminating infarct-related VT. Ablating the tissue in which the two I-shaped scroll wave filaments sustaining the VTs in FIG. 2 resided also resulted in VT non-inducibility. The larger GZ (and thus longer filaments) required more extensive ablation lesions to encompass the filaments.

FIG. 4B shows ablation of only one of the two filaments sustaining reentry in FIG. 2, resulting in failure to terminate all VTs. Following ablation, the modified morphology and size of the GZ resulted in VT being sustained by a different I-type filament, with ends attached to the scar and epicardium.

The simulations described above demonstrate that accurate identification of the optimal ablation targets in each individual heart could be carried out by determining, by means of individual MRI-based heart modeling, the locations of all scroll-wave filaments that sustain VT in the particular MI heart. Ablating the tissue in which the filaments resided successfully terminates all VTs. The simulation results also demonstrate that even when the first ablation attempt could be unsuccessful (because of, for instance, the filaments being difficult to fully access by an endo- or epicardial catheter approach in the EP lab), the new ablation targets (new filaments) associated with the modified VT substrate (modified GZ morphology and size) can be calculated again from the model, providing a dynamic update of the optimal ablation targets.

Sensitivity of VT Filaments to GZ Model Parameters

The simulation results described above clearly demonstrate the paramount role that the GZ plays in establishing the locations, number and type of the scroll-wave filament(s) that sustain monomorphic VT in the MI heart. Since the filaments are the optimal ablation targets, accurate identification of their spatial positioning in each individual heart is key to the clinical translation of this simulation-guidance-of-VT-ablation approach. In the models presented here, GZ is represented as a homogenous region characterized with average electrophysiological remodeling (homogenous changes in ionic currents and conductivities, the latter resulting from Cx43 downregulation and lateralization). However, histological examinations of infracted tissue have shown that voxels identified as GZ from MR scans correspond to microscopically heterogeneous mixtures of viable myocardium and infarct scar (H. Arheden, M. Saeed, C. B. Higgins, D. W. Gao, P. C. Ursell, J. Bremerich, R. Wyttenbach, M. W. Dae, M. F. Wendland, Reperfused rat myocardium subjected to various durations of ischemia: estimation of the distribution volume of contrast material with echo-planar MR imaging *Radiology*. 215, 520-528 (2000)). Representing GZ as a heterogeneous region would significantly complicate the model. Most importantly, the degree of GZ heterogeneity is difficult to assess from MRI scans, which would render the clinical utility of the simulation guidance approach to VT ablation difficult to ascertain. Therefore, we performed simulations to determine the sensitivity of the spatial position of the VT filaments to the degree of GZ structural heterogeneity.

Similarly, we represent the ionic current remodeling in the GZ as a set of homogeneous ion current conductance changes, with specific data derived from the extensive literature on the canine epicardial border zone properties, as described in Methods. However, ionic current downregulation could be different in different animal species and the human, and data may not be readily available; furthermore, there could be significant variability in GZ ionic current remodeling between individual hearts. Demonstrating that physiological variations in GZ ionic current remodeling do not affect the accurate prediction of scroll-wave filaments by our modeling approach makes the clinical translation of the approach feasible because it eliminates the need to obtain information about the GZ electrophysiological properties in each individual heart. Therefore, we also performed simulations to determine the sensitivity of the spatial position of the VT filaments to the degree of ionic current remodeling in the GZ.

In both sets of simulations, we deemed the spatial position of the VT filaments not sensitive to a particular set of GZ model parameters when this position remained within the approximate volume of a single clinical ablation lesion. As shown by Lardo et al (A. C. Lardo, E. R. McVeigh, P. Jumrussirikul, R. D. Berger, H. Calkins, J. Lima, H. R. Halperin, Visualization and temporal/spatial characterization of cardiac radiofrequency ablation lesions using magnetic resonance imaging Circulation. 102, 698-705 (2000)), the size of a typical single ablation lesion is 9.4±0.05 mm by 6.7±0.05 mm by 3.4±2.1 mm.

Figures 5A, 5B, 5C, 5D, 5E, 5F:
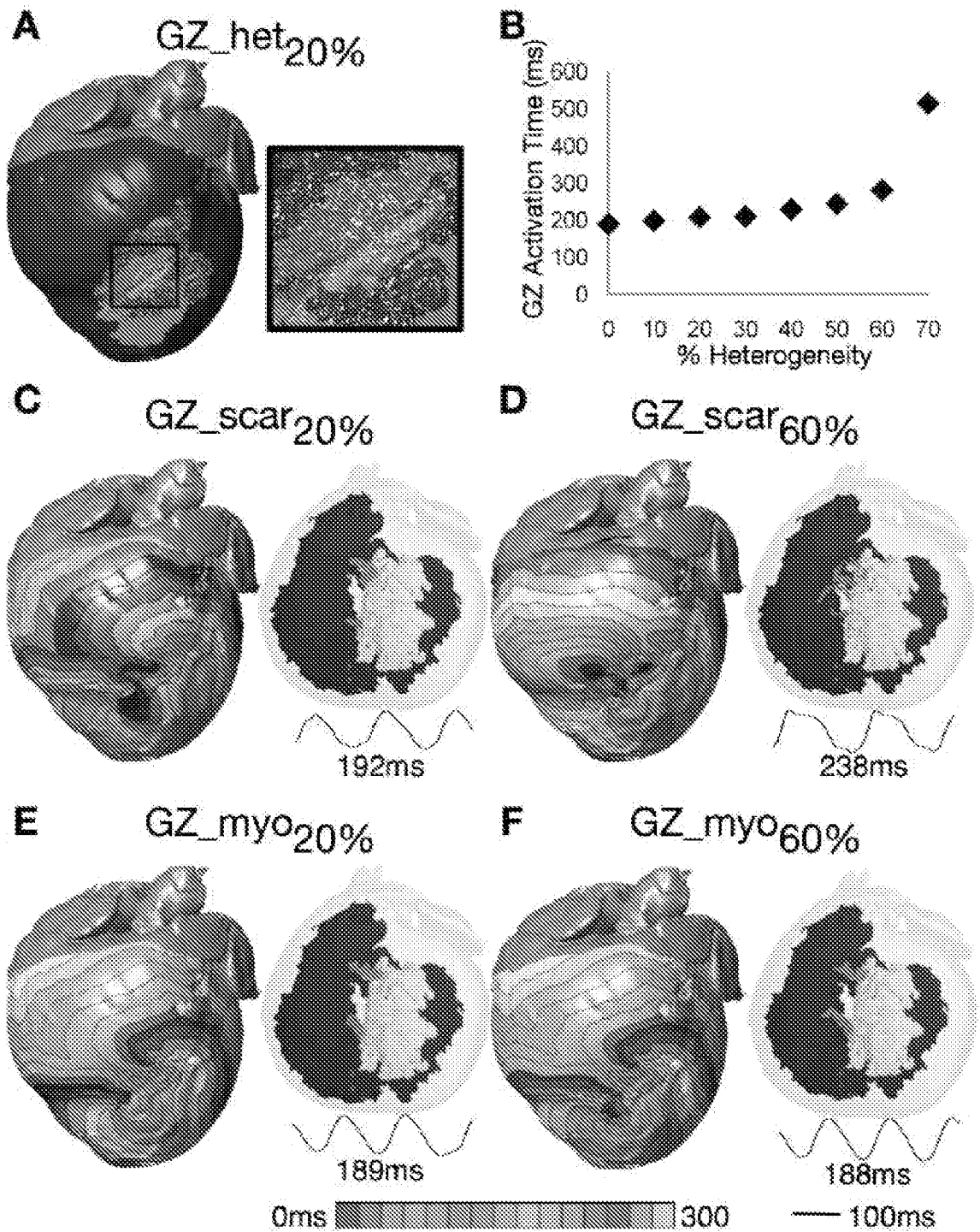
FIGS. 5A-5F show sensitivity of filament position to GZ electrophysiological properties. A. Model with 20% scar in GZ (white speckles). B. Time needed to fully activate GZ as a function of scar density in GZ. C. and D. Activation maps, filaments, and pseudo-ECGs for GZs composed of 20% and 60% scar. E. and F. Same for GZ composed of 20% and 60% normal myocardium.

In the first set of simulations, micro-regions of scar were randomly distributed in the models throughout the GZ volume at varying densities (10% to 90% of GZ volume in 10% steps, FIG. 5A shows the 20% case), although histological studies have demonstrated that scar infiltration in the GZ is only up to 40% of GZ volume (H. Arheden, M. Saeed, C. B. Higgins, D. W. Gao, P. C. Ursell, J. Bremerich, R. Wyttenbach, M. W. Dae, M. F. Wendland, Reperfused rat myocardium subjected to various durations of ischemia: estimation of the distribution volume of contrast material with echo-planar MR imaging Radiology. 215, 520-528 (2000)). Following PES, the locations of the resulting filaments were compared to those in the corresponding homogeneous GZ model. Incorporation of scar in the GZ resulted in conduction slowing within GZ. The total time it took to fully activate the GZ increased with increased degree of scar density (FIG. 5B). For the heterogeneous cases with GZ composed of up to 40% scar, all induced VT morphologies were identical to that in control (FIG. 2B). FIG. 5C shows the activation maps and filament locations for the model that incorporated 20% scar in the GZ. VT cycle length was 2% longer than in control, with VT again manifested as a figure-of-eight reentry on the epicardium and breakthrough on the endocardium. Most importantly, the filaments remained in the same spatial position, with accuracy fully within one clinical lesion.

As GZ scar density increased to more than 70%, wavefronts did not fully propagate through GZ, rendering it functionally identical to the scar; VT was also not inducible. In FIG. 5D (60% scar), VT cycle length was 26% longer than in control. The VT was manifested as 6 reentries on the epicardium, with multiple filaments densely packed within the GZ. Despite the more complex VT spatiotemporal dynamics, filaments remained within the same general area as in control.

In the second set of simulations, we similarly incorporated random micro-regions in the GZ at increasing density, this time composed of normal myocardium. The simulations revealed that models with unchanged GZ conductivities but GZ composition incorporating up to 80% normal tissue exhibited the same VT morphology as in control; VT cycle lengths also did not differ significantly from the control (188.1±0.76 ms). Increasing the amount of GZ normal tissue to 90% and 100% rendered VTs non-inducible. FIGS. 5E-5F show the activation maps and filament locations for the VTs induced in models with 20% and 60% normal tissue in GZ. In both cases, there were slight changes in the activation pattern within the GZ as compared to control, but the reentrant patterns remained the same. Again, the filaments remained in the same spatial position, with accuracy within one clinical lesion.

These simulations demonstrate that scroll-wave filament locations are not particularly sensitive to the composition of the GZ and are determined predominately by GZ morphology and size. The results also strengthen significantly the possibility of clinical translation of the proposed "virtual EP lab" approach for identifying the optimal VT ablation targets since they demonstrate that the approach needs only the acquisition of the clinical MR and a model with "average" electrophysiological properties.

Predicting the Optimal Ablation Targets: a Retrospective Animal Study

To demonstrate that our modeling approach can successfully be used to predict the optimal ablation targets, we conducted a retrospective animal study. Five pigs underwent intracardiac electrophysiological (EP) study to ablate post-MI VT; in-vivo MRIs with LGE pre- and post-ablation were also acquired (see Methods). Of the five hearts, ablation succeeded and VT was non-inducible during a follow up EP study 1 week post-ablation; in the other 3, ablation failed. All swine hearts were reconstructed from the in-vivo MRI scans, ventricular electrophysiological models created, and PES simulated to determine arrhythmogenicity, VT morphology, and filament locations.

Figures 6A, 6B, 6C, 6D, 6E, 6F:
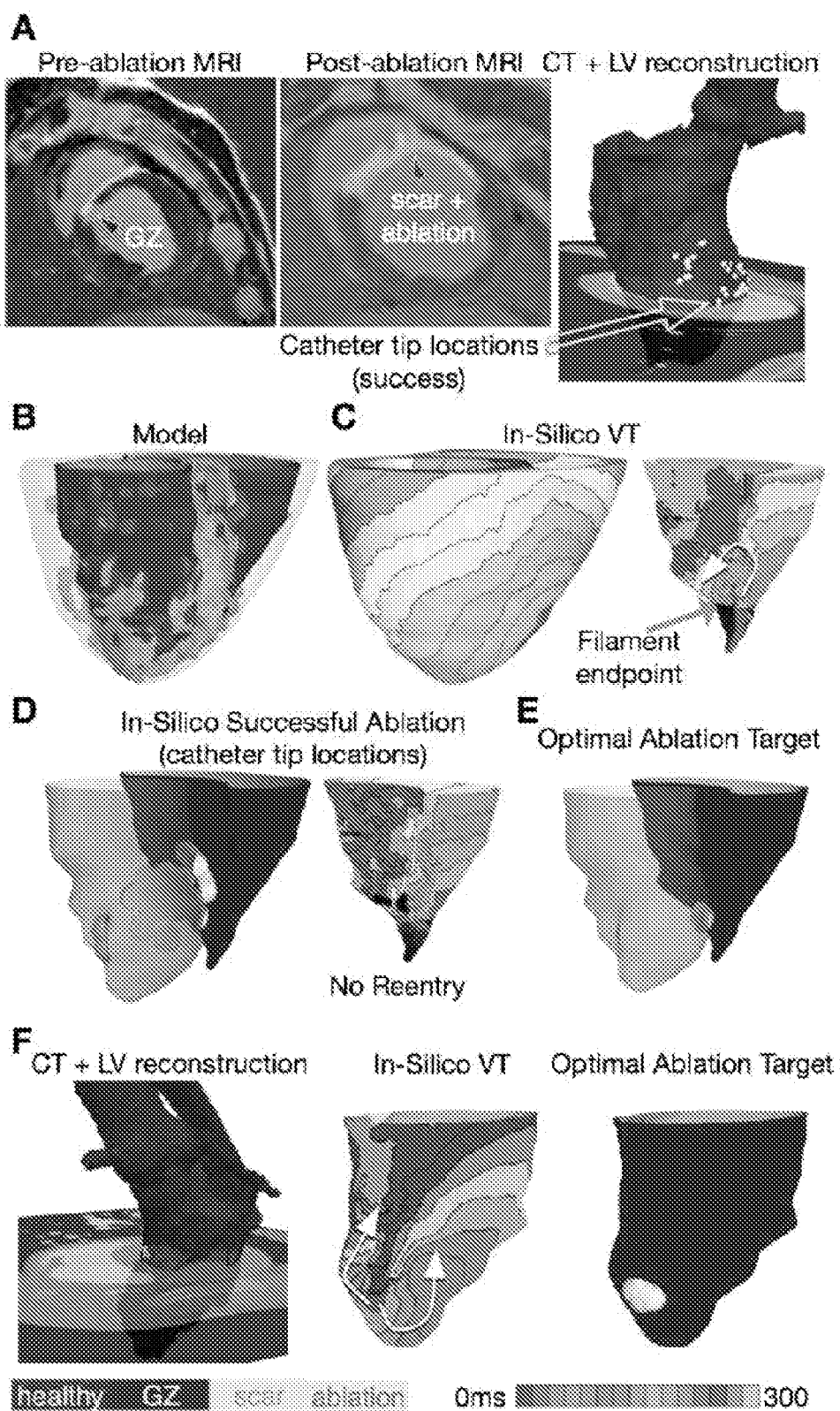
FIGS. 6A-6F show retrospective validation of successful ablation in swine hearts according to an embodiment of the current invention. A. Pre- and post-ablation in-vivo MRI; reconstruction of LV endocardium from CT (rendered semi-transparently) with the locations of catheter tip (white dots). B. Model reconstructed from pre-ablation MRI (epicardium and GZ rendered semi-transparent). C. Simulated VT activation map, with reentry organized around a filament with endpoints on the RV side of septum and scar. D. Incorporating experimental ablation in the model also results in VT non-inducibility. E. Targeted ablation of the filament renders VT non-inducible. F. Another example of heart with successful VT ablation. Corresponding VT simulation and predicted optimal ablation target are also shown.

FIG. 6 presents experimental and simulation results for the two hearts where post-MI VT was chronically ablated. FIG. 6A shows pre- and post-ablation MRIs of one pig heart, as well as the LV endocardium reconstructed from CT with the locations of the catheter tip delivering ablation (white dots) registered on the endocardial surface. In this heart, lesions were created throughout the septum, successfully terminating VT. Comparing pre- and post-ablation MRIs demonstrated that the ablated region co-localized with the GZ in the septum (FIG. 6A). The computational model accurately reconstructed the septal infarct with islands of viable GZ (FIG. 6B). Following PES, the induced VT organized around an I-type filament located on the septum with endpoints on the RV endocardium and scar (FIG. 6C). Implementing in the model the experimental lesions also successfully terminated VT (FIG. 6D), demonstrating excellent correspondence between model and experiment. However, the experimental ablation lesions were fairly extensive (FIG. 6D). The simulations demonstrated that a smaller ablation lesion at the location of the filament would have successfully terminated VT (FIG. 6E).

FIG. 6F shows another example of excellent correspondence between experiment and simulation prediction. In this animal, ablation delivered at a relatively small area on the septum chronically rendered VT non-inducible. The simulations revealed that the presence of GZ in this area resulted in the formation of two I-type filaments; thus this region was the optimal ablation target.

Figures 7A, 7B, 7C, 7D, 7E, 7F:
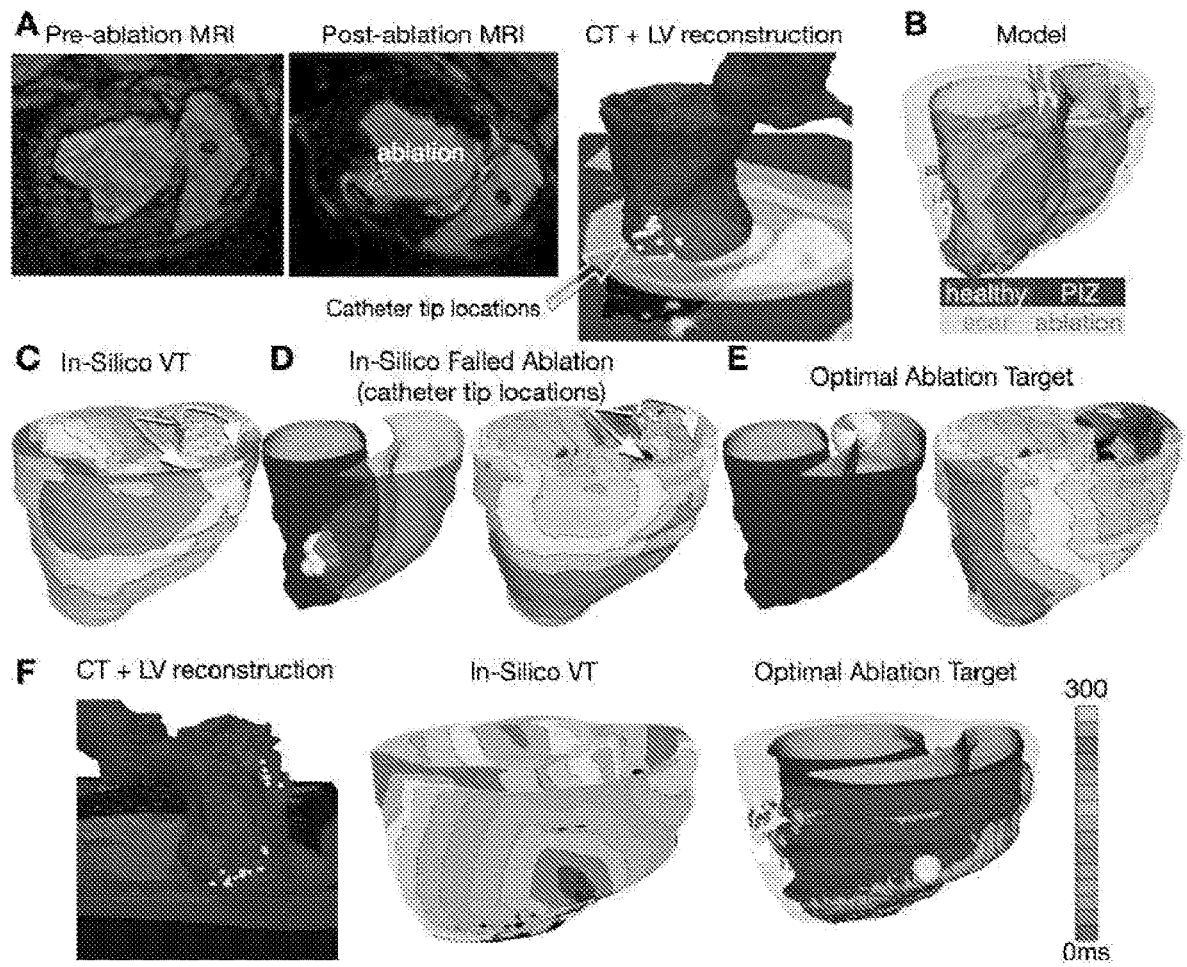
FIGS. 7A-7F show retrospective validation of failed ablation in swine hearts. A. Pre- and post-ablation in-vivo MRI; reconstruction of LV endocardium from CT. B. Model reconstruction (epi- and endocardium rendered semi-transparent). C. Simulated VT activation map, with reentry figure-of-eight reentry on anterior RV. D. Incorporating experimental ablation in the model also results in ablation failure. E. Simulation-predicted optimal ablation target. F. Another example of heart with failed ablation with corresponding simulated MI-related VT and predicted optimal ablation target.

For the three animals where VT was not chronically ablated, the post-ablation MRI revealed that ablation was not delivered at the GZ. FIG. 7A shows that in one animal the heart was ablated along the posterior portion of the LV wall near the RV insertion point. MRI with LGE post-ablation revealed that the lesions were distal from the infarct, the latter located primarily at the septum and anterior portion of the LV (FIG. 7A). Using the pre-ablation reconstruction shown in FIG. 7B and simulating PES revealed that reentry was organized around two I-type filaments in the GZ located at the anterior portion of the RV (FIG. 7C). Simulations that incorporated the experimental ablation lesions correctly predicted that VT would remain inducible (FIG.

7D), with morphology similar to pre-ablation. Ablating the site of filament formation at the GZ in the RV resulted in ablation success in-silico (FIG. 7E).

FIG. 7F shows another example where experimental ablation was delivered at sites distal from the GZ. In this case, the heart was ablated at the anterior LV wall near the RV insertion point and the LV free wall near the base. The simulations correctly predicted VT termination failure when the experimental lesions were incorporated in the model. Modeling was able to determine that GZ in RV harbored the filaments and was the optimal ablation target. Similar was the case of failed ablation in the third pig (results not shown).

Discussion

Ventricular ablation is currently offered to MI patients with recurrent infarct-related VT. A catheter is inserted through veins for an endocardial approach to map the electrical activity of the heart following an arrhythmia induction protocol, so that the targets of ablation can be identified (E. M. Aliot, W. G. Stevenson, J. M. Almendral-Garrote, F. Bogun, C. H. Calkins, E. Delacretaz, P. D. Bella, G. Hindricks, P. Jais, M. E. Josephson, J. Kautzner, G. N. Kay, K.-. Kuck, B. B. Lerman, F. Marchlinski, V. Reddy, M.-. Schalij, R. Schilling, K. Soejima, D. Wilber, EHRA/HRS Expert Consensus on Catheter Ablation of Ventricular Arrhythmias: Developed in a partnership with the European Heart Rhythm Association (EHRA), a Registered Branch of the European Society of Cardiology (ESC), and the Heart Rhythm Society (FIRS); in collaboration with the American College of Cardiology (ACC) and the American Heart Association (AHA) *Europace.* 11, 771 <lastpage> 817 (2009; 2009)). Mapping is a meticulous process, lasting for several hours, in which information regarding the electrical activity on the ventricular surface is collected from the tip of a roving catheter on a point-by-point basis (J. Brugada, A. Berruezo, A. Cuesta, J. Osca, E. Chueca, X. Fosch, L. Wayar, L. Mont, Nonsurgical transthoracic epicardial radiofrequency ablation: an alternative in incessant ventricular tachycardia. *J. Am. Coll. Cardiol.* 41, 2036-2043 (2003); E. Sosa, M. Scanavacca, A. d'Avila, F. Oliveira, J. A. Ramires, Nonsurgical transthoracic epicardial catheter ablation to treat recurrent ventricular tachycardia occurring late after myocardial infarction. *J. Am. Coll. Cardiol.* 35, 1442-1449 (2000)). The generated maps are thus typically of low resolution, and the propagation pathways, as identified from the maps, are only surface manifestations of the 3D reentrant circuits during infarct-related VT. Furthermore, mapping is best performed during sustained VT. However, patients often exhibit a hemodynamic intolerance to the sustained VT induced in the EP lab, which does not allow the time needed for detailed mapping. Therefore, infarct-related VT ablation remains a relatively high-risk procedure with a success rate far from desired (D. J. Callans, E. Zado, B. H. Sarter, D. Schwartzman, C. D. Gottlieb, F. E. Marchlinski, Efficacy of radiofrequency catheter ablation for ventricular tachycardia in healed myocardial infarction. *Am. J. Cardiol.* 82, 429-432 (1998)).

The above examples demonstrate some concepts of a non-invasive approach to identify the optimal infarct-related VT ablation targets according to an embodiment of the current invention. This embodiment includes using, prior to the clinical procedure, an MRI-based subject-specific multiscale electrophysiological model of the heart to analyze post-MI VT circuits and to determine the optimal ablation targets. The approach allows for a full 3D visualization and analysis of these circuits. As the results of the present study demonstrate, the optimal ablation targets are the scroll-wave filaments that sustain VTs, which were found to be stably located in the GZ. Once the optimal ablation targets are determined and visualized by the present approach, ablation delivery could be swift and precise, eradicating, with a minimal number of lesions, all infarct-related VTs. This will dramatically improve the efficacy of ablation, increase the tolerance for the procedure, and reduce post-procedure complications and long-term deleterious effects resulting from the lengthy invasive mapping and the numerous unnecessary ablation lesions. Translating the approach presented here into the clinic will constitute a dramatic shift in the paradigm of infarct-related VT ablation procedure.

Importantly, the approach presented here allows for careful ablation procedure planning. It is possible that the locations of the scroll-wave filaments are not accessible, in their entirety, by any clinical endo- or epicardial approach. The subject-specific heart model could then be used to play out scenarios of tiered ablation approaches, where the filament locations are re-calculated following an initial model ablation that does not eradicate all filaments, much like in FIG. 4B. Such targeted "filament modification" approach (electrophysiologically equivalent to a targeted GZ substrate modification) in situations of restricted access to the sites will still terminate all VTs with a minimum number of ablation lesions.

The predictive capabilities of the approach were tested here in a retrospective animal study. We demonstrated that when the experimental lesions resulting in VT termination were implemented in the model, the latter also predicted VT termination; similarly, failed ablation in the experiment was also a failure to ablate VT in the model. Importantly, comparisons between experimental ablation lesions that eradicated VT and the optimal ablation lesions predicted by the model revealed that ablation could have succeeded with a much smaller number of ablations and an overall lesion size that is dramatically smaller than the one delivered in the experiment (FIG. 6).

A novel mechanistic insight from the results presented is that the scroll-wave filaments sustaining infarct-related monomorphic VT (i.e. the optimal ablation targets) are fully contained within the GZ; the simulation results also provided information regarding how GZ size determines filament type. GZ was thus the arrhythmogenic substrate that promoted wavebreak and reentry formation. Our findings are consistent with observations of epicardial reentrant activity anchored to regions of slow conduction within GZ, made during electrical mapping of post-MI VT (H. Ashikaga, T. Sasano, J. Dong, M. M. Zviman, R. Evers, B. Hopenfeld, V. Castro, R. H. Helm, T. Dickfeld, S. Nazarian, J. K. Donahue, R. D. Berger, H. Calkins, M. R. Abraham, E. Marban, A. C. Lardo, E. R. McVeigh, H. R. Halperin, Magnetic resonance-based anatomical analysis of scar-related ventricular tachycardia: implications for catheter ablation *Circ. Res.* 101, 939-947 (2007)). Similarly, recent clinical studies using contrast-enhanced cardiac MRI have shown that GZ extent correlates with arrhythmia susceptibility in patients with ischemic cardiomyopathy (A. Schmidt, C. F. Azevedo, A. Cheng, S. N. Gupta, D. A. Bluemke, T. K. Foo, G. Gerstenblith, R. G. Weiss, E. Marban, G. F. Tomaselli, J. A. Lima, K. C. Wu, Infarct tissue heterogeneity by magnetic resonance imaging identifies enhanced cardiac arrhythmia susceptibility in patients with left ventricular dysfunction. *Circulation.* 115, 2006-2014 (2007); A. T. Yan, A. J. Shayne, K. A. Brown, S. N. Gupta, C. W. Chan, T. M. Luu, M. F. Di Carli, H. G. Reynolds, W. G. Stevenson, R. Y. Kwong, Characterization of the peri-infarct zone by contrast-enhanced cardiac magnetic resonance imaging is a powerful predictor of post-myocardial infarction mortality. *Circulation.* 114, 32-39 (2006); S. D. Roes, C. J. Borleffs, R. J. van der Geest, J. J. Westenberg, N. A. Marsan, T. A. Kaandorp, J. H. Reiber, K. Zeppenfeld, M. J. Lamb, A. de Roos, M. J. Schalij, J. J. Bax, Infarct tissue heterogeneity assessed with contrast-enhanced MRI predicts spontaneous ventricular arrhythmia in patients with ischemic cardiomyopathy and implantable cardioverter-defibrillator *Circ. Cardiovasc. Imaging.* 2, 183-190 (2009)). The filament locations in GZ were found to not be sensitive to the structural composition of the GZ. Our simulations show that the presence of up to 40% of scar in GZ does not affect filament spatial position; even with 70% scar in GZ, the induced VTs still had filaments located in approximately the same general region as in the model without scar tissue in GZ (FIG. 5C-5D). The filaments spatial position was also not much sensitive to the degree of ionic current remodeling in GZ. For a given PES site, GZ morphology and size were found to be the main determinants of filament number, location, and type. Our simulations demonstrated that approximating the GZ as a homogeneously remodeled tissue with slowed conduction is sufficient to predict the locations of post-MI VT filaments.

The "virtual EP lab" presented here incorporates advanced image-processing for in-vivo MRI-based subject-specific heart model generation as well as sophisticated numerical simulation and analysis approaches. Should the methodology be successfully implemented in the clinic, it will constitute a major leap forward in the integration of computational modeling, traditionally a basic-science discipline, in the diagnosis and treatment of cardiac disease.

In conclusion, we presented examples of a novel approach for accurate identification of infarct-related VT ablation targets according to an embodiment of the current invention. In this example, we focused on monomorphic VT, and demonstrated the predictive capabilities of the approach in a retrospective animal study.

Methods

Datasets and Model Creation

Ex-Vivo Canine Heart:

Details regarding the image acquisition and reconstruction of the infarcted canine heart from ex-vivo MRI and DTMRI images were fully described elsewhere (F. Vadakkumpadan, H. Arevalo, A. J. Prassl, J. Chen, F. Kickinger, P. Kohl, G. Plank, N. Trayanova, Image-based models of cardiac structure in health and disease *Wiley Interdisciplinary Reviews Systems Biology and Medicine.* 2, 489-506 (2010)).

In-Vivo Swine Hearts:

The infarcted swine hearts imaging and EP study were previously described (H. L. Estner, M. M. Zviman, D. Herzka, F. Miller, V. Castro, S. Nazarian, H. Ashikaga, Y. Dori, R. D. Berger, H. Calkins, A. C. Lardo, H. R. Halperin, The Critical Isthmus Sites of Ischemic Ventricular Tachycardia are in Zones of Tissue Heterogeneity, Visualized by Magnetic Resonance Imaging *Heart Rhythm.* (2011) (H. L. Estner, M. M. Zviman, D. Herzka, F. Miller, V. Castro, S. Nazarian, H. Ashikaga, Y. Dori, R. D. Berger, H. Calkins, A. C. Lardo, H. R. Halperin, The Critical Isthmus Sites of Ischemic Ventricular Tachycardia are in Zones of Tissue Heterogeneity, Visualized by Magnetic Resonance Imaging *Heart Rhythm.* (2011)). For this example, we used a subset of the datasets (5 pigs) to prospectively validate our simulation methodology. In these pigs, MI was induced via occlusion of the mid-left anterior descending coronary artery. Four weeks after MI induction, the animals underwent in-vivo contrast-enhanced MRI at a resolution of $976 \times 976 \times 4000$ µm$^3$. One day post-MRI, the animals underwent a full EP study to ablate VT. 7-9 days post-ablation, the animals underwent a follow up EP study to determine if ablation resulted in VT non-inducibility. A post-ablation in-vivo MRI was also performed.

FIGS. 1D-1F illustrate the reconstruction of hearts from pre-ablation in-vivo MRI. First, ventricles were segmented from the rest of the torso by fitting closed splines through a set of landmark points placed manually along the epi- and endocardial boundaries (FIG. 1D). These splines were then tricubically interpolated to obtain a segmentation of the ventricles with a resolution of $400 \times 400 \times 400$ um$^3$. To segment the infarct, the MR images were tricubically interpolated to the same resolution as the ventricular segmentation. Gray-level thresholding was used to segment healthy myocardium, infarct scar, and GZ (A. Schmidt, C. F. Azevedo, A. Cheng, S. N. Gupta, D. A. Bluemke, T. K. Foo, G. Gerstenblith, R. G. Weiss, E. Marban, G. F. Tomaselli, J. A. Lima, K. C. Wu, Infarct tissue heterogeneity by magnetic resonance imaging identifies enhanced cardiac arrhythmia susceptibility in patients with left ventricular dysfunction. *Circulation.* 115, 2006-2014 (2007)). We used software tools developed by our group to create finite element meshes of the hearts that incorporated adaptive element sizing that preserves fine details of the geometry including infarct surfaces.

Electrophysiological Parameters:

In healthy ventricular myocardium, passive electrical properties were defined using normal conductivity values (L. Clerc, Directional differences of impulse spread in trabecular muscle from mammalian heart. *J. Physiol.* (Lond.). 255, 335-346 (1976)) and ionic kinetics were described by the Luo-Rudy II model of ventricular action potential (C. Luo, Y. Rudy, A dynamic model of the cardiac ventricular action potential. II. Afterdepolarizations, triggered activity, and potentiation. *Circ Res.* 74, 1097-1113 (1994)) (FIG. 1G). The GZ incorporated experimentally determined changes that resulted in decreased transverse conductivity (J. Yao, W. Hussain, P. Patel, N. Peters, P. Boyden, A. Wit, Remodeling of gap junctional channel function in epicardial border zone of healing canine infarcts. *Circ. Res.* 92, 437-443 (2003)) and action potential with decreased excitability and increased duration (J. Pu, P. Boyden, Alterations of Na$^+$ currents in myocytes from epicardial border zone of the infarcted heart. A possible ionic mechanism for reduced excitability and postrepolarization refractoriness. *Circ. Res.* 81, 110-119 (1997); W. Dun, S. Baba, T. Yagi, P. A. Boyden, Dynamic remodeling of K+ and Ca2+ currents in cells that survived in the epicardial border zone of canine healed infarcted heart. *Am. J. Physiol. Heart Circ. Physiol.* 287, H1046-54 (2004); M. Jiang, C. Cabo, J. Yao, P. Boyden, G. Tseng, Delayed rectifier K currents have reduced amplitudes and altered kinetics in myocytes from infarcted canine ventricle. *Cardiovasc. Res.* 48, 34-43 (2000)).

Simulation Protocol and Analysis

Mathematical description of cardiac tissue was based on monodomain equations. The software CARP was used to solve this system of equations on a parallel computing system (E. Vigmond, M. Hughes, G. Plank, L. J. Leon, Computational tools for modeling electrical activity in cardiac tissue. *J. Electrocardiol.* 36, 69-74 (2003)).

To classify the induced VT morphologies, pseudo-ECGs were calculated by taking the difference of extracellular potentials between two points separated by 18 cm in an isotropic bath surrounding the hearts. The extracellular potentials were approximated using an integral equation by Gima et al (K. Gima, Y. Rudy, Ionic Current Basis of Electrocardiographic Waveforms: A Model Study. *Circ Res.* 90, 889-896 (2002)).

Scroll-wave filaments were determined by converting transmembrane potential maps into phase angle maps, and then determining the nodes where the integral of the phase angles of surrounding nodes was ±2π (C. Larson, L. Dragnev, N. Trayanova, Analysis of electrically-induced reentrant circuits in a sheet of myocardium. *Ann Biomed Eng.* 31, 768-80 (2003)). These nodes correspond to locations of phase singularities, which are the filament building blocks.

Some other aspects of the current invention are directed computational models of ventricular electromechanics in providing a new level of understanding of the relationship between electrical and mechanical activation in the heart, and how this understanding can be utilized to provide improved cardiac resynchronization therapy (CRT) strategies.

Dyssynchronous Heart Failure

Heart failure is a major cardiovascular disease affecting 5 million people in the US alone, and is associated with high morbidity and mortality rates (Lloyd-Jones et al., 2009). (The references cited in the following examples are listed below for convenience.) The syndrome is characterized with impaired pump function due to the deleterious remodeling of the ventricles, from the organ down to the molecular level, which significantly alters the electrical and mechanical behavior of the heart. High-resolution magnetic resonance imaging (MRI) and diffusion tensor (DT) MRI scans (Helm et al., 2006) have shown that in dyssynchronous heart failure (DHF) there is a substantial remodeling of ventricular geometry and structure. At the organ level, the ventricles become dilated and wall thickness is reduced. At the tissue level, laminar sheet angle is altered, and the transmural gradient in fiber orientation is increased. Because chamber geometry and sheet structure are major determinants of LV mechanics (Cheng et al., 2008; LeGrice et al., 1995), the mechanical deformation of the failing heart is markedly different. Furthermore, altered heart geometry as well as fiber and sheet orientations directly affect 3D electrical propagation (Hooks et al., 2007) in the failing heart.

Heart failure is also characterized with remodeling of the electrophysiological and mechanical properties at the cellular and subcellular levels. Studies (Akar et al., 2007; Akar et al., 2004) have shown that the gap junctional protein connexin43 (Cx43) is redistributed from the intercalated disk to the lateral myocyte borders and that the amount of hypophosphorylated Cx43 is increased, leading to reduced conduction velocity in heart failure. There is a considerable downregulation of the membrane potassium channels carrying the Ito and IK1 currents (Kaab et al., 1996) and of the intracellular Ca2+ ATPase (SERCA) pump (O'Rourke et al., 1999), and upregulation of the Na—Ca exchanger (NCX) (O'Rourke et al., 1999). Remodeled ionic currents and Ca2+ handling result in altered Ca2+ transients, which, in turn, impair active tension development by the myofilaments in the cell. Finally, differential expression of collagen isoforms (Marijianowski et al., 1995) and altered ratio of titin (Wu et al., 2002) (an intrasarcomeric protein that modulates myofilament passive tension) isoforms results in increased myocardial stiffness.

Because of the combined effects of chamber, contractile, and electrophysiological remodeling, the ability of the LV to efficiently pump blood is severely compromised in heart failure patients. Furthermore, a subset of these patients exhibits abnormal electrical conduction that delays activation of one portion of the ventricle relative to another (intraventricular conduction delay due to left bundle branch block, LBBB). This results in contractile dyssynchrony (dyssynchronous heart failure, DHF), which further diminishes cardiac systolic function and energetic efficiency.

Cardiac Resynchronization Therapy

CRT is an established therapy for DHF patients. CRT typically employs bi-V pacing, with an endocardial right ventricular (RV) pacing lead and an epicardial LV pacing lead, to re-coordinate contraction (Bleeker et al., 2006a). CRT has been shown to acutely and chronically improve systolic function (Nelson et al., 2000) of the heart and to reverse the detrimental remodeling (Sutton et al., 2006) associated with heart failure. Clinical trials of CRT have consistently demonstrated improvement in heart failure symptoms, exercise tolerance, quality of life, and a reduction in recurrent hospitalizations (Auricchio et al., 2003).

Although CRT reduces morbidity and mortality (Cleland et al., 2005), approximately 30% of patients fail to respond to the therapy (Kass, 2005). This reflects the poor predictive capability of current approaches to identify potential responders to CRT. The QRS duration (QRS≥150 ms), widely used in clinical trials as a basic component of the inclusion criteria for CRT, does not provide an indication of the degree of mechanical dyssynchrony (Fauchier et al., 2003). Indeed, patients with long QRS duration may not exhibit mechanical dyssynchrony and those with short QRS complexes may present with significant dyssynchrony in contraction (Auricchio et al., 1999; Fauchier et al., 2002; Pitzalis et al., 2002). Measurements of mechanical dyssynchrony by Doppler echocardiography (Bax et al., 2004; Yu et al., 2002) reveal only local dyssynchrony, while the complex deformations in DHF are global. In recent clinical trials, Doppler echocardiography was characterized by lack of repeatability and low predictive value (Beshai et al., 2007; Chung et al., 2008; Miyazaki et al.). The poor predictive capability of the above measures indicates an incomplete understanding of the relation between the electrical and mechanical events in DHF.

The presence of myocardial infarction (MI) is an additional reason for lack of response to CRT. Placement of a pacing electrode at or near the infarct scar may result in ineffective pacing and thus in failure of resynchronization. Since infarction modulates electromechanical interactions, it also alters the mechanism of CRT. Bleeker et al. (Bleeker et al., 2006b) documented that patients with transmural posterolateral scar have a much lower response rate to CRT than those without scar, 14% vs. 81%. Increased scar volume has been found to result in unfavorable response to CRT (Adelstein and Saba, 2007). Infarct location and scar transmurality are considered important (Choi et al., 2001; White et al., 2006) yet unknown factors that affect the relationship between electrical activation and contraction and contribute to diminished CRT efficacy.

Finally, the location of LV pacing has been shown to play an important role in CRT efficacy (Butter et al., 2000; Helm et al., 2007; St John Sutton et al., 2003). Currently, LV pacing lead is implanted in a tributary of the coronary sinus, as in epicardial bi-V pacing (Butter et al., 2001). However, for a small class of patients unsuitable for transvenous bi-V, a transseptal approach has been developed that allows endocardial bi-V pacing (Leclercq et al., 1999). Recent studies have brought to light the potential proarrhythmic effect of epicardial bi-V pacing (Fish et al., 2005), resulting from the reversal of the direction of electrical propagation in the LV. Furthermore, new findings indicate that endocardial bi-V pacing might be associated with improved resynchronization in canine models (Howard et al., 2011; van Deursen et al., 2009) and humans (Spragg et al., 2010). Thus determining the optimal location of LV pacing lead placement remains a problem.

Multi-scale computational modeling of electromechanics in the normal and failing heart is provided to address these problems according to some embodiments of the current invention. Recent advancements in cardiac computational modeling, numerical algorithms and image processing techniques have enabled the development of detailed tomographically-reconstructed heart models that integrate functions from the molecular level to the electromechanical interactions in the intact organ. According to this embodiment of the current invention, we employ such models to provide approaches to optimizing CRT therapy. To achieve this goal, this embodiment focuses on exploiting knowledge regarding the electromechanical delay in the heart as well as myocardial efficiency.

Electromechanical Delay in the Heart and how it can be Used to Optimize CRT

Significance of Electromechanical Delay

The time period between the local electrical depolarization and the onset of local myofiber shortening (mechanical activation) in the intact ventricles can last as much as tens of milliseconds. This electromechanical delay (EMD) is a function of the myocyte's intrinsic latent period between membrane depolarization and myofilament activation in the excitation-contraction process (Cordeiro et al., 2004), but is also dependent on the local myofiber mechanical loading conditions in the intact heart. Acute CRT therapy affects only the component of EMD that is due to the loading conditions, but has no influence on the cell-intrinsic E-C coupling latency (Russell et al., 2011). Thus, by understanding EMD and its distribution that is due to the loading conditions, one could suggest potential avenues for CRT optimization. Alternatively, since most echocardiography-based dyssynchrony measurements are affected by the timing of myofiber shortening onset, ascertaining the mechanisms underlying the EMD distribution may improve or lead to the development of novel indices of electromechanical dyssynchrony to identify potential CRT responders.

Electromechanical Delay in the Normal Heart

The first computational study to assess the 3D distribution of EMD was by Usyk and McCulloch (Usyk and McCulloch, 2003). In this study, the authors employed an electromechanical model of the normal canine ventricles to determine the 3D EMD distribution during sinus rhythm and following LV pacing. With this early model, which in fact was the first whole-heart electromechanical model developed, the authors demonstrated that EMD may be both positive and negative, indicating that myofiber shortening may precede electrical activation in the whole heart. A more recent study by Gurev et al. (Gurev et al., 2010) have expounded on this work by providing thorough analysis of the 3D EMD distribution in the normal rabbit heart and its dependence on the loading conditions (i.e. on the electrical activation sequence). Simulations of electromechanical activity during sinus rhythm and LV epicardial pacing were conducted and compared to determine the effect of electrical activation pattern on the 3D distribution of EMD. The simulation results revealed that the 3D distribution of EMD was heterogeneous and depended on the electrical activation sequence. The distributions were markedly different for sinus rhythm and epicardial pacing. During sinus rhythm, the distribution was longer at the epicardium compared to the endocardium and longer at the base compared to the apex. Following epicardial pacing, the distribution was markedly different: the posterior wall exhibited longer EMD compared to the anterior wall. Mechanistic analysis of the electromechanical behavior revealed that the late-depolarized regions were characterized with significant myofiber pre-stretch caused by the contraction of the early-depolarized regions. This pre-stretch, in turn, delayed myofiber shortening onset, and resulted in longer EMD there.

Assessment of EMD in DHF

The pumping inefficiency of the DHF heart arises from deleterious remodeling of cardiac electromechanical properties, from the sub-cellular to the organ level, and is thus expected to change the 3D EMD distribution. Determining the 3D EMD distribution in the setting of DHF and exploiting the mechanistic insight into the relation between electrical activation and mechanical contraction could offer clues to improvement in CRT delivery. In this section, we present our new image-based electromechanical model of the failing canine ventricles, and employ it to determine how the 3D distribution of EMD is altered in the setting of DHF according to an embodiment of the current invention.

Figure 8:
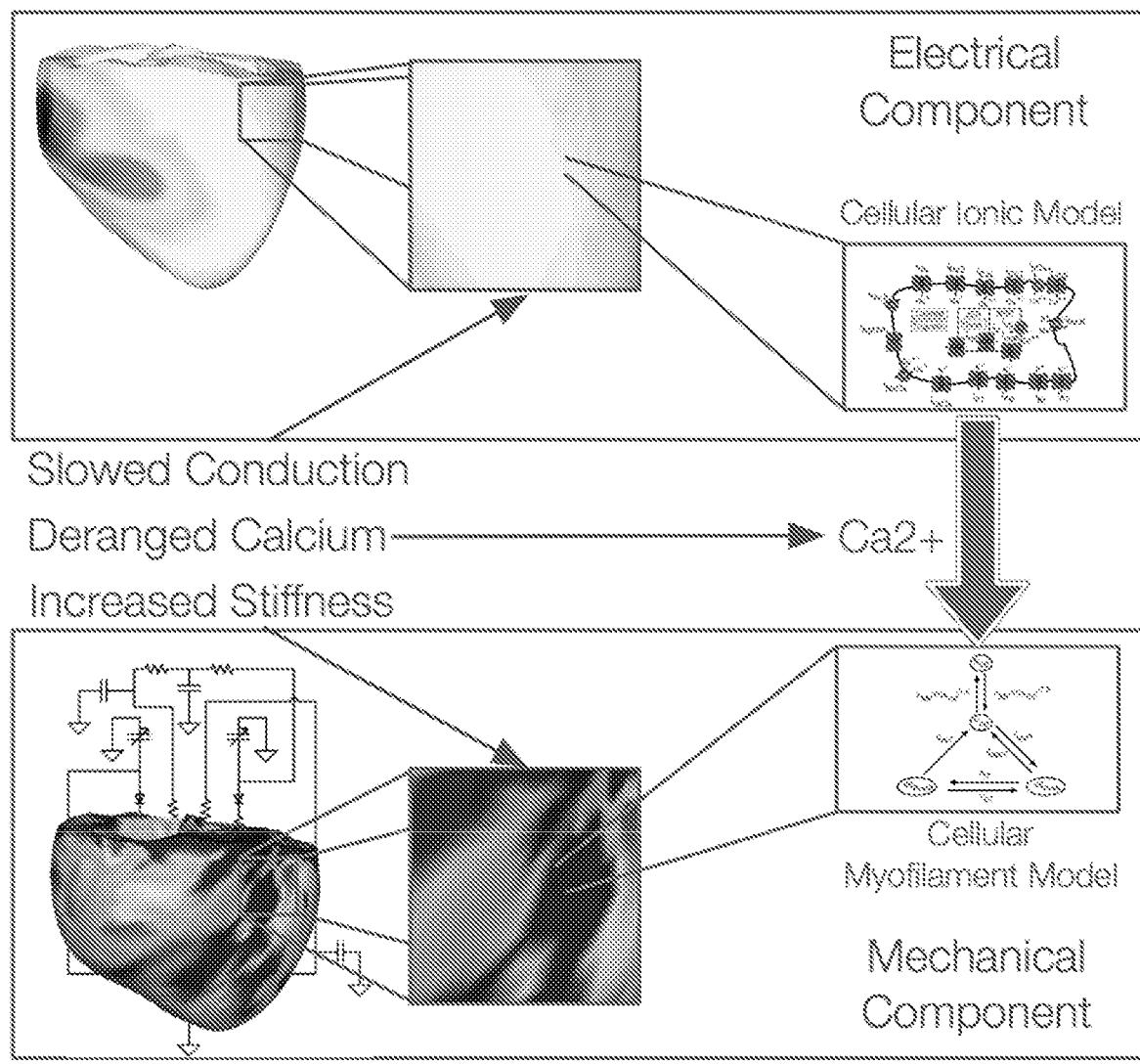
FIG. 8 is a schematic illustration of an overall approach to image-based modeling of DHF electromechanics according to an embodiment of the current invention. The geometrical images of hearts in the electrical and mechanical components are of the remodeled DHF canine heart. The light blue arrows indicate where the remodeling aspects of slowed conduction, deranged calcium, increased stiffness were incorporated into the model.

A schematic of the electromechanical model of the failing heart is shown in FIG. 8. Briefly, the electromechanical model is composed of two main components, an electrical and a mechanical component. The electrical component, which contains a biophysically-detailed representation of myocyte membrane kinetics, simulates the propagation of the action potential, while the mechanical component, which incorporates a biophysical model of myofilament dynamics, describes the active contraction and resultant deformation of the ventricles. Details regarding the basics of the model pertaining to the normal ventricles can be found in (Gurev et al., 2011). The model is generic, and could be used with any geometry, image-based or idealized. In the studies presented in this section, the geometry of the electromechanical model was generated from MR images of DHF canine ventricles (FIG. 8), and the fiber and sheet architecture were constructed from DTMR images of the same DHF canine ventricles, using a recently developed methodology (Gurev et al., 2011). Using MR and DTMR images for the reconstruction of the DHF ventricular geometry and fiber and sheet geometry allows for the inclusion of the structural remodeling of the DHF ventricles.

To take into account the remodeling of the passive electromechanical tissue properties associated with DHF, the following changes were incorporated into the model (FIG. 8). First, electrical conductivities were reduced by 20% from the normal values to represent the slowed conduction in DHF (Akar et al., 2004). To account for the increased stiffness of the failing myocardial tissue (Wu et al., 2002), the passive scaling constant in the strain—energy function was increased fivefold. Finally, to incorporate deranged calcium handling associated with the DHF heart (O'Rourke et al., 1999), the peak amplitude and relaxation rate of the calcium transient function, which served as an input model of the myofilament dynamics (Rice et al., 2008), was reduced to 70% and increased by 30% of the normal values, respectively. Since CRT patients exhibit a left bundle branch block (LBBB) type of electrical activation, LBBB was simulated in both models by stimulating the endocardial surface at discrete locations as if the electrical activity was emanating from the activation of the corresponding branch of the Purkinje network.

Figures 9A, 9B, 9C:
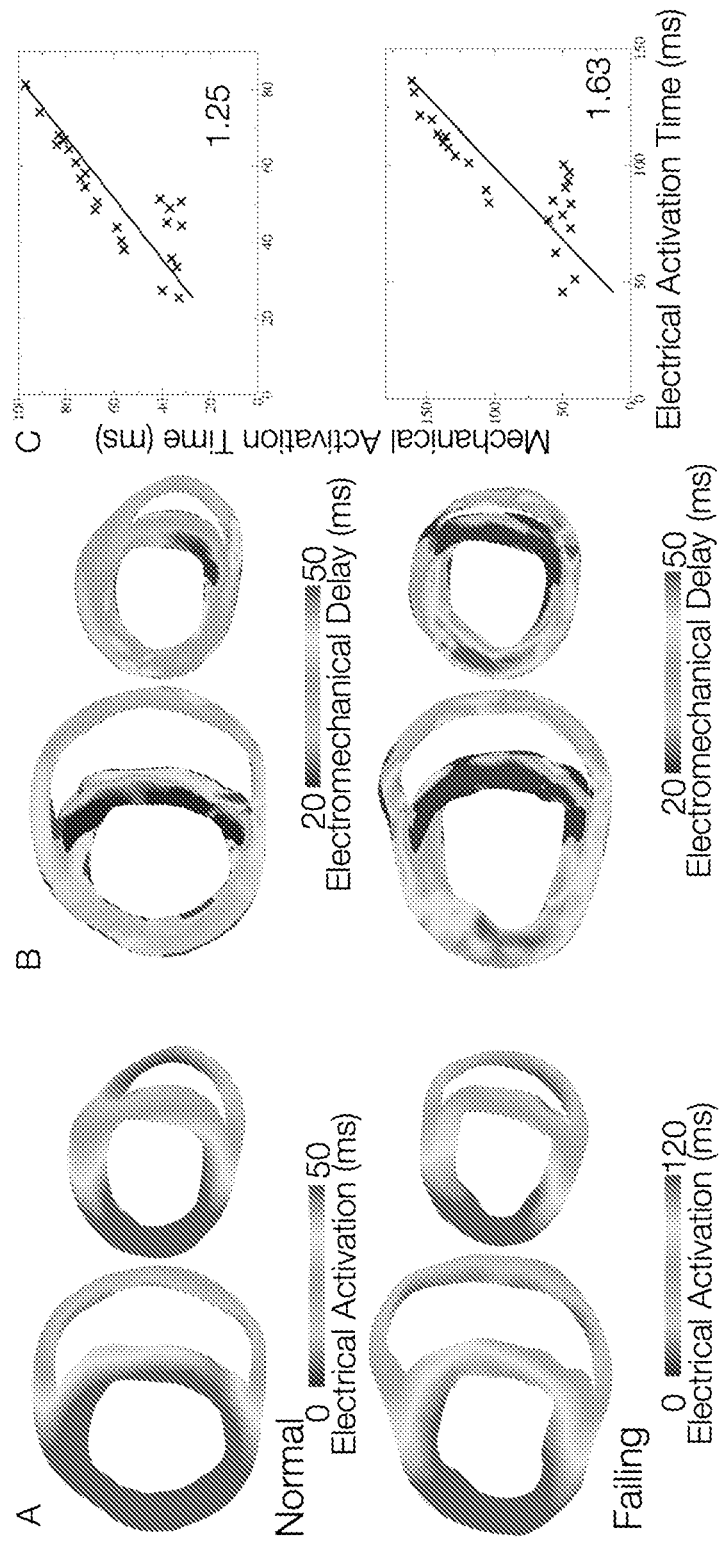
FIG. 9A shows transmural short-axis electrical maps during LBBB for normal (top) and DHF (bottom) hearts.
FIG. 9B shows transmural short-axis EMD maps during LBBB for normal (top) and DHF (bottom) hearts.
FIG. 9C shows correlation between electrical activation and mechanical activation time during LBBB for normal (top) and DHF (bottom) hearts.

FIG. 9A presents the transmural electrical activation map in LBBB for the DHF heart in a short axis view; the same map for the normal canine heart but with LBBB is also shown. This comparison allows the examination of the differences in electrical activation that arise from heart failure remodeling. In both hearts the depolarization wave travels from the right ventricular wall, through the septum and to the left ventricular lateral wall; the mechanical activation follows the same general direction (data not shown). The electromechanical activation patterns are consistent with previous experimental results (Becker et al., 1958; Leclercq et al., 2002). To assess the contribution of the detrimental remodeling associated with DHF to altering the 3D EMD distribution, the resultant transmural EMD maps for the normal and DHF hearts are compared in FIG. 9B. The maps reveal that the 3D EMD distribution is heterogeneous in both the normal and failing hearts: the late-activated lateral wall is associated with an extended EMD as compared to the septum. However, in the DHF heart, EMD is longer that in the normal heart. The differences in EMD are particularly pronounced at the lateral wall (green in normal vs red in DHF, FIG. 9B).

To further examine the relationship between electrical and mechanical activation in DHF, the electrical and mechanical activation times at 24 different locations in the left ventricular mid-wall in the normal and DHF canine ventricles are presented in FIG. 9C. A linear regression analysis was performed. The slopes of the regression lines, which were obtained through least squares fitting, are greater than 1 in the normal and DHF hearts, indicating that the time interval between depolarization and onset of myofiber shortening is extended at the late-activated regions. However, this interval increases at a greater rate in the DHF heart (1.25 vs 1.63). These data demonstrate that the detrimental changes to the electromechanical properties in the DHF heart results in a prolonged EMD, particularly at the LV anterior wall during LBBB activation sequence.

Initial Modeling Efforts Towards the Assessment of Contractile Dyssynchrony and EMD in the Infarcted Heart As mentioned above, the presence of MI is also expected to alter the EMD distribution in the ventricles. This section presents the initial modeling effort towards constructing an electromechanical model of the infarcted ventricles, which could be used to then assess the distribution of EMD in MI, and suggest possible improvements in CRT therapy in DHF patients with ischemic cardiomyopathy.

The model was reconstructed from MRI and DTMRI scans of canine ventricles with a 4-week old infarct. Briefly, the zone of infarct was segmented from the healthy myocardium using the fractional anisotropy values calculated from the DTMRI data, and the infarct zone was then divided into the akinetic scar and the partially viable peri-infarct using level set thresholding. Further details regarding the infarct segmentation can be found in Vadakkumpadan et al. (Vadakkumpadan et al., 2010). The mechanics finite elements mesh is shown in FIG. 10A; the infarct zone (scar with peri-infarct), is demarcated in blue.

Because the scar is primarily composed of necrotic collagen, it was modeled as an insulator in the electrical component of the model. In the mechanics component of the model, the passive stiffness constant was increased 1500% and no active tension was generated in the scar. In the peri-infarct, the transverse electrical conductivity was reduced by 90% to reflect the disorganization of Cx43. To account for the mechanical changes in the peri-infarct, the active tension was reduced to 10% and the passive stiffness constant was increased fifteen fold (Tyberg et al., 1970; Walker et al., 2005).

An example simulation of paced propagation using the MRI-based electromechanical model of the infarcted canine ventricles is shown in FIG. 10B. Owing to the tethering of the adjacent myocardium to the akinetic scar, myocyte shortening was impaired at the LV anterior wall, resulting in regional dyssynchrony. These data suggest that the EMD distribution in the MI heart will be markedly altered by the presence of an infarct; this distribution will depend on the specific scar location and transmurality. Electromechanical models with realistic topography of MI can be used to construct 3D maps of EMD for various scar locations and degrees of transmurality to reveal the mechanisms by which infarction alter the electromechanical activity of the heart.

Using the EMD Distribution to Guide CRT Optimization

Suboptimal placement of the LV lead constitutes a major reason underlying the high non-response rate to CRT. To date, there is no clear consensus as to where to place the LV pacing lead to achieve optimal CRT response. Previous studies (Ansalone et al., 2002; Howard et al., 2011; Suffoletto et al., 2006) have indicated that the site of latest electrical or the latest mechanical activation was associated with a greater hemodynamic benefit to CRT; however, recent data (Derval et al., 2010; Fung et al., 2009; Spragg et al., 2010) suggests there is a lack of concordance between the site of latest electrical or mechanical activation and CRT response. In a pilot study (abstract) by Constantino et al. (Constantino et al., 2010), we proposed an alternative strategy to determine the LV pacing location in an effort to optimize the response to CRT: targeting the regions with the longest EMD. This section presents simulation results towards optimization of CRT employing this strategy. Using the image-based model of canine DHF electromechanics, as described above, CRT was delivered by pacing at the RV apex, with the LV pacing electrode placed at 18 different epicardial sites along the LV free wall. For each LV pacing site, response to CRT was assessed by calculating the percent change in maximal rise in LV pressure ($dP/dt_{max}$) as compared to that in the DHF heart.

Using the transmural EMD maps that were constructed as described above, the region with the longest EMD was determined to be the endocardial surface of the lateral wall between the base and the mid-ventricles during LBBB. FIG. 11A presents CRT response as a function of LV pacing location. Maximal hemodynamic benefit occurred when the LV pacing site was located near the base and mid-ventricle, which was within the region of longest EMD. The relationship between LV pacing location and longest EMD region is quantified in FIG. 11B. For each pacing site, CRT response and the longitudinal distance between the pacing site and the center of the region with the longest EMD were plotted. Increase in $dP/dt_{max}$ strongly correlated with the longitudinal distance between LV pacing site and the center of the region with longest EMD ($r=-0.86$, $p<0.05$).

These computational results demonstrate that targeting the region with the longest EMD results in greatest hemodynamic response to CRT. Thus determining the 3D EMD distribution in DHF could be used to guide the optimal placement of the LV pacing electrode for CRT. It remains to be determined whether the same approach will be applicable in the infarcted heart, where discord between electrical and mechanical activity is exacerbated by the presence of the infarct (Ashikaga et al., 2005).

Using Energy Consumption as a Guide to CRT Optimization

An alternative approach to identify the optimal LV pacing location for CRT may be to target the LV location that results in maximum increase in myocardial efficiency while simultaneously minimizing the heterogeneity in energy consumption. This suggestion is based on the fact that myocardial efficiency, the ratio of mechanical work performed by the ventricles to myocardial energy consumption, is markedly reduced in DHF patients (Suga, 1990). Furthermore, it has been shown that CRT improves myocardial efficiency in DHF patients (Lindner et al., 2006). Since current experimental techniques are limited by the inability to record local mechanical activity and energy consumption in the ventricles with high spatiotemporal resolution, subject-specific electromechanical models of the DHF ventricles that incorporate a biophysically-detailed representation of cardiac myofilament dynamics can be employed to analyze the effect of CRT on local energy consumption and total myocardial efficiency in the setting of DHF and potentially identify the optimal LV pacing location. Below we present such results.

Simulations of LBBB and CRT were performed using the MRI-based electromechanical model of DHF canine heart, as above. The use of the Rice et al. (Rice et al., 2008) representation of myofilament dynamics allowed for the calculation of local energy consumption. ATP consumption distribution was calculated by integrating over time the ATP consumption rate, a function of the ATP-consuming cross-bridge detachment rate and the single overlap fraction of thick filaments. The ATP consumption of the entire ventricle was then determined by spatially integrating the local ATP consumption throughout the entire ventricular volume, as done in our previous publication (Lim et al., 2012). Finally, mechanical work was calculated by integrating the area within the pressure-volume loop curve generated by the model, and myocardial efficiency was calculated as the ratio of mechanical work to total ATP consumption in the ventricles.

Figure 12A:
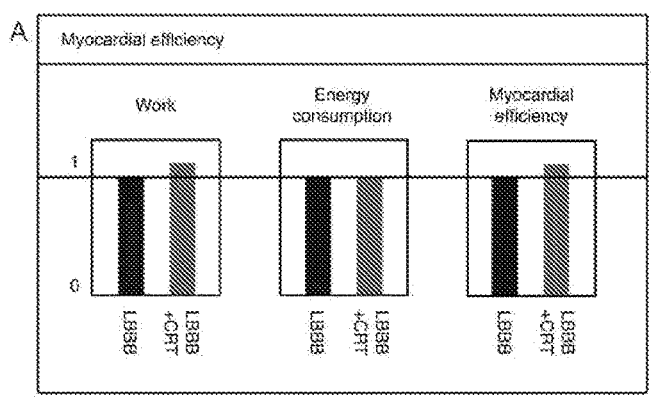
FIG. 12A is a bar graph of stroke work (left), total ventricular energy consumption (middle) and myocardial efficiency (right) during LBBB and following CRT. Values are normalized to LBBB values.
Figure 12B:
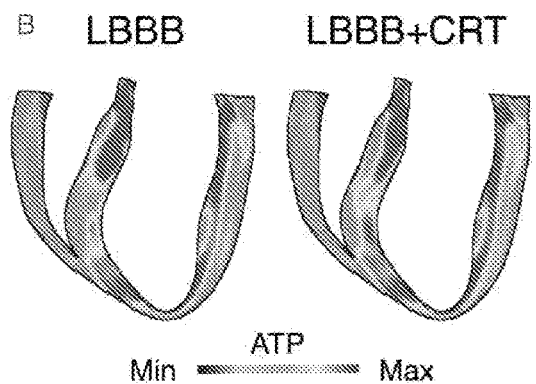
FIG. 12B shows distribution of ATP consumption during LBBB and following CRT.

Consistent with experimental findings (Lindner et al., 2006; Lindner et al., 2005; Ukkonen et al., 2003), CRT resulted in improvement in myocardial efficiency (FIG. 12A). This stems from the fact that CRT increased the mechanical work performed by the ventricles without increasing the total ventricular energy consumption. Although total energy consumption was unaltered, CRT homogenized energy consumption throughout the ventricles by increasing energy consumption at the septum and reducing it at the lateral wall (FIG. 12A); this finding is consistent with experimental data (Lindner et al., 2006; Lindner et al., 2005; Ukkonen et al., 2003). These results demonstrate that computational models of DHF electromechanics can accurately simulate the effects of CRT on myocardial efficiency and local energy consumption and can be used to determine the LV pacing location that minimizes the heterogeneity in energy consumption and maximizes myocardial efficiency.

Conclusions Regarding CRT Examples

A comprehensive characterization of the spatiotemporal electromechanical interactions in the DHF heart, without and with MI, is fundamental to the effort towards improving CRT efficacy. This example demonstrates that a biophysically-based model of ventricular electromechanics that incorporates representations from the scale of the protein to the intact organ is a powerful methodology to provide insight into the electromechanical interactions in the heart. This example highlights how the basic science insight into the electromechanical activity of the DHF heart gained from computational modeling can be exploited to guide improvements in CRT delivery according to an embodiment of the current invention. The simulation results presented here indicate that optimal CRT strategy in the DHF heart can be achieved by pacing at the LV location characterized with longest EMD. The same approach can be used to determine whether CRT can be also optimized by targeting the region with the longest EMD in the infarcted heart. In addition, computational modeling could also aid in the identification of the LV pacing location that results in maximal myocardial efficiency and most beneficial regional energy consumption. With new advancements in computational modeling and increased ubiquity of computers in the clinic, it will not be long before electromechanical models of DHF patients' hearts that are enriched with patient-specific data will serve as a bedside tool for diagnosis and treatment planning.

Adelstein, E. C. and Saba, S. (2007) Scar Burden by Myocardial Perfusion Imaging Predicts Echocardiographic Response to Cardiac Resynchronization Therapy in Ischemic Cardiomyopathy. *Am Heart J* 153, 105-12.

Akar, F. G., Nass, R. D., Hahn, S., Cingolani, E., Shah, M., Hesketh, G. G., DiSilvestre, D., Tunin, R. S., Kass, D. A. and Tomaselli, G. F. (2007) Dynamic Changes in Conduction Velocity and Gap Junction Properties During Development of Pacing-Induced Heart Failure. *Am J Physiol Heart Circ Physiol* 293, H1223-30.

Akar, F. G., Spragg, D. D., Tunin, R. S., Kass, D. A. and Tomaselli, G. F. (2004) Mechanisms Underlying Conduction Slowing and Arrhythmogenesis in Nonischemic Dilated Cardiomyopathy. *Circ Res* 95, 717-25.

Ansalone, G., Giannantoni, P., Ricci, R., Trambaiolo, P., Fedele, F. and Santini, M. (2002) Doppler myocardial imaging to evaluate the effectiveness of pacing sites in patients receiving biventricular pacing. *J Am Coll Cardiol* 39, 489-99.

Ashikaga, H., Mickelsen, S. R., Ennis, D. B., Rodriguez, I., Kellman, P., Wen, H. and McVeigh, E. R. (2005) Electromechanical analysis of infarct border zone in chronic myocardial infarction. *Am J Physiol Heart Circ Physiol* 289, H1099-105.

Auricchio, A., Stellbrink, C., Block, M., Sack, S., Vogt, J., Bakker, P., Klein, H., Kramer, A., Ding, J., Salo, R., Tockman, B., Pochet, T. and Spinelli, J. (1999) Effect of Pacing Chamber and Atrioventricular Delay on Acute Systolic Function of Paced Patients with Congestive Heart Failure. The Pacing Therapies for Congestive Heart Failure Study Group. The Guidant Congestive Heart Failure Research Group. *Circulation* 99, 2993-3001.

Auricchio, A., Stellbrink, C., Butter, C., Sack, S., Vogt, J., Misier, A. R., Bocker, D., Block, M., Kirkels, J. H., Kramer, A. and Huvelle, E. (2003) Clinical Efficacy of Cardiac Resynchronization Therapy Using Left Ventricular Pacing in Heart Failure Patients Stratified by Severity of Ventricular Conduction Delay. *J Am Coll Cardiol* 42, 2109-16.

Bax, J. J., Bleeker, G. B., Marwick, T. H., Molhoek, S. G., Boersma, E., Steendijk, P., van der Wall, E. E. and Schalij, M. J. (2004) Left Ventricular Dyssynchrony Predicts Response and Prognosis after Cardiac Resynchronization Therapy. *J Am Coll Cardiol* 44, 1834-40.

Becker, R. A., Scher, A. M. and Erickson, R. V. (1958) Ventricular excitation in experimental left bundle branch block. *Am Heart J* 55, 547-56.

Beshai, J. F., Grimm, R. A., Nagueh, S. F., Baker, J. H., Beau, S. L., Greenberg, S. M., Pires, L. A. and Tchou, P. J. (2007) Cardiac-resynchronization therapy in heart failure with narrow QRS complexes. *N Eng J Med* 357, 2461-2471.

Bleeker, G. B., Bax, J. J., Steendijk, P., Schalij, M. J. and van der Wall, E. E. (2006a) Left Ventricular Dyssynchrony in Patients with Heart Failure: Pathophysiology, Diagnosis and Treatment. *Nat Clin Pract Cardiovasc Med* 3, 213-9.

Bleeker, G. B., Kaandorp, T. A., Lamb, H. J., Boersma, E., Steendijk, P., de Roos, A., van der Wall, E. E., Schalij, M. J. and Bax, J. J. (2006b) Effect of Posterolateral Scar Tissue on Clinical and Echocardiographic Improvement after Cardiac Resynchronization Therapy. *Circulation* 113, 969-76.

Butter, C., Auricchio, A., Stellbrink, C., Fleck, E., Ding, J., Yu, Y., Huvelle, E. and Spinelli, J. (2001) Effect of Resynchronization Therapy Stimulation Site on the Systolic Function of Heart Failure Patients. *Circulation* 104, 3026-9.

Butter, C., Auricchio, A., Stellbrink, C., Schlegl, M., Fleck, E., Horsch, W., Huvelle, E., Ding, J. and Kramer, A. (2000) Should Stimulation Site Be Tailored in the Individual Heart Failure Patient? *Am J Cardiol* 86, 144K-151K.

Cheng, A., Nguyen, T. C., Malinowski, M., Daughters, G. T., Miller, D. C. and Ingels, N. B. (2008) Heterogeneity of left ventricular wall thickening mechanisms. *Circulation* 118, 713-721.

Choi, K. M., Kim, R. J., Gubernikoff, G., Vargas, J. D., Parker, M. and Judd, R. M. (2001) Transmural Extent of Acute Myocardial Infarction Predicts Long-Term Improvement in Contractile Function. *Circulation* 104, 1101-7.

Chung, E. S., Leon, A. R., Tavazzi, L., Sun, J. P., Nihoyannopoulos, P., Merlino, J., Abraham, W. T., Ghio, S., Leclercq, C. and Bax, J. J. (2008) Results of the Predictors of Response to CRT (PROSPECT) trial. *Circulation* 117, 2608-2616.

Cleland, J. G., Daubert, J. C., Erdmann, E., Freemantle, N., Gras, D., Kappenberger, L. and Tavazzi, L. (2005) The Effect of Cardiac Resynchronization on Morbidity and Mortality in Heart Failure. *N Engl J Med* 352, 1539-49.

Constantino, J., Gurev, V. and Trayanova, N. (2010) Optimal cardiac resynchronization therapy is achieved by pacing from the LV region with the longest electromechanical delay. *Heart Rhythm* 7, S164-165.

Cordeiro, J. M., Greene, L., Heilmann, C., Antzelevitch, D. and Antzelevitch, C. (2004) Transmural heterogeneity of calcium activity and mechanical function in the canine left ventricle. *Am J Physiol Heart Circ Physiol* 286, H1471-9.

Derval, N., Steendijk, P., Gula, L. J., Deplagne, A., Laborderie, J., Sacher, F., Knecht, S., Wright, M., Nault, I., Ploux, S., Ritter, P., Bordachar, P., Lafitte, S., Reant, P., Klein, G. J., Narayan, S. M., Garrigue, S., Hocini, M., Haissaguerre, M., Clementy, J. and Jais, P. (2010) Optimizing hemodynamics in heart failure patients by systematic screening of left ventricular pacing sites: the lateral left ventricular wall and the coronary sinus are rarely the best sites. *J Am Coll Cardiol* 55, 566-75.

Fauchier, L., Marie, O., Casset-Senon, D., Babuty, D., Cosnay, P. and Fauchier, J. P. (2002) Interventricular and Intraventricular Dyssynchrony in Idiopathic Dilated Cardiomyopathy: A Prognostic Study with Fourier Phase Analysis of Radionuclide Angioscintigraphy. *J Am Coll Cardiol* 40, 2022-30.

Fauchier, L., Marie, O., Casset-Senon, D., Babuty, D., Cosnay, P. and Fauchier, J. P. (2003) Reliability of QRS Duration and Morphology on Surface Electrocardiogram to Identify Ventricular Dyssynchrony in Patients with Idiopathic Dilated Cardiomyopathy. *Am J Cardiol* 92, 341-4.

Fish, J. M., Brugada, J. and Antzelevitch, C. (2005) Potential Proarrhythmic Effects of Biventricular Pacing. *J Am Coll Cardiol* 46, 2340-7.

Fung, J. W., Lam, Y. Y., Zhang, Q., Yip, G. W., Chan, W. W., Chan, G. C., Chan, J. Y. and Yu, C. M. (2009) Effect of left ventricular lead concordance to the delayed contraction segment on echocardiographic and clinical outcomes after cardiac resynchronization therapy. *J Cardiovasc Electrophysiol* 20, 530-5.

Gurev, V., Constantino, J., Rice, J. J. and Trayanova, N. A. (2010) Distribution of electromechanical delay in the heart: insights from a three-dimensional electromechanical model. *Biophys J* 99, 745-54.

Gurev, V., Lee, T., Constantino, J., Arevalo, H. and Trayanova, N. A. (2011) Models of cardiac electromechanics based on individual hearts imaging data: image-based electromechanical models of the heart. *Biomech Model Mechanobiol* 10, 295-306.

Helm, P. A., Younes, L., Beg, M. F., Ennis, D. B., Leclercq, C., Faris, 0. P., McVeigh, E., Kass, D., Miller, M. I. and Winslow, R. L. (2006) Evidence of Structural Remodeling in the Dyssynchronous Failing Heart. *Circ Res* 98, 125-32.

Helm, R. H., Byrne, M., Helm, P. A., Daya, S. K., Osman, N. F., Tunin, R., Halperin, H. R., Berger, R. D., Kass, D. A. and Lardo, A. C. (2007) Three-Dimensional Mapping of Optimal Left Ventricular Pacing Site for Cardiac Resynchronization. *Circulation* 115, 953-61.

Hooks, D. A., Trew, M. L., Caldwell, B. J., Sands, G. B., LeGrice, I. J. and Smaill, B. H. (2007) Laminar Arrangement of Ventricular Myocytes Influences Electrical Behavior of the Heart. *Circ Res* 101, e 103-12.

Howard, E. J., Covell, J. W., Mulligan, L. J., McCulloch, A. D., Omens, J. H. and Kerckhoffs, R. C. (2011) Improvement in pump function with endocardial biventricular pacing increases with activation time at the left ventricular pacing site in failing canine hearts. *Am J Physiol Heart Circ Physiol* 301, H1447-55.

Kaab, S., Nuss, H. B., Chiamvimonvat, N., O'Rourke, B., Pak, P. H., Kass, D. A., Marban, E. and Tomaselli, G. F. (1996) Ionic Mechanism of Action Potential Prolongation in Ventricular Myocytes from Dogs with Pacing-Induced Heart Failure. *Circ Res* 78, 262-73.

Kass, D. A. (2005) Cardiac Resynchronization Therapy. *J Cardiovasc Electrophysiol* 16 Suppl 1, S35-41.

Leclercq, C., Faris, O., Tunin, R., Johnson, J., Kato, R., Evans, F., Spinelli, J., Halperin, H., McVeigh, E. and Kass, D. A. (2002) Systolic improvement and mechanical resynchronization does not require electrical synchrony in the dilated failing heart with left bundle-branch block. *Circulation* 106, 1760-3.

Leclercq, F., Hager, F. X., Macia, J. C., Mariottini, C. J., Pasquie, J. L. and Grolleau, R. (1999) Left Ventricular Lead Insertion Using a Modified Transseptal Catheterization Technique: A Totally Endocardial Approach for Permanent Biventricular Pacing in End-Stage Heart Failure. *Pacing Clin Electrophysiol* 22, 1570-5.

LeGrice, I. J., Takayama, Y. and Covell, J. W. (1995) Transverse Shear Along Myocardial Cleavage Planes Provides a Mechanism for Normal Systolic Wall Thickening. *Circ Res* 77, 182-93.

Lindner, O., Sorensen, J., Vogt, J., Fricke, E., Baller, D., Horstkotte, D. and Burchert, W. (2006) Cardiac efficiency and oxygen consumption measured with 11C-acetate PET after long-term cardiac resynchronization therapy. *J Nucl Med* 47, 378-83.

Lindner, O., Vogt, J., Kammeier, A., Wielepp, P., Holzinger, J., Bailer, D., Lamp, B., Hansky, B., Korfer, R., Horstkotte, D. and Burchert, W. (2005) Effect of cardiac resynchronization therapy on global and regional oxygen consumption and myocardial blood flow in patients with non-ischaemic and ischaemic cardiomyopathy. *Eur Heart J* 26, 70-6.

Lloyd-Jones, D., Adams, R., Carnethon, M., De Simone, G., Ferguson, T. B., Flegal, K., Ford, E., Furie, K., Go, A., Greenlund, K., Haase, N., Hailpern, S., Ho, M., Howard, V., Kissela, B., Kittner, S., Lackland, D., Lisabeth, L., Marelli, A., McDermott, M., Meigs, J., Mozaffarian, D., Nichol, G., O'Donnell, C., Roger, V., Rosamond, W., Sacco, R., Sorlie, P., Stafford, R., Steinberger, J., Thom, T., Wasserthiel-Smoller, S., Wong, N., Wylie-Rosett, J. and Hong, Y. (2009) Heart Disease and Stroke Statistics-2009 Update: A Report from the American Heart Association Statistics Committee and Stroke Statistics Subcommittee. *Circulation* 119, 480-6.

Marijianowski, M. M., Teeling, P., Mann, J. and Becker, A. E. (1995) Dilated Cardiomyopathy Is Associated with an Increase in the Type I/Type III Collagen Ratio: A Quantitative Assessment. *J Am Coll Cardiol* 25, 1263-72.

Miyazaki, C., Redfield, M. M., Powell, B. D., Lin, G. M., Herges, R. M., Hodge, D. O., Olson, L. J., Hayes, D. L., Espinosa, R. E., Rea, R. F., Bruce, C. J., Nelson, S. M., Miller, F. A. and Oh, J. K. (2010) Dyssynchrony indices to predict response to cardiac resynchronization therapy: a comprehensive prospective single-center study. *Circ Heart Fail* 3, 565-73.

Nelson, G. S., Berger, R. D., Fetics, B. J., Talbot, M., Spinelli, J. C., Hare, J. M. and Kass, D. A. (2000) Left Ventricular or Biventricular Pacing Improves Cardiac Function at Diminished Energy Cost in Patients with Dilated Cardiomyopathy and Left Bundle-Branch Block. *Circulation* 102, 3053-9.

O'Rourke, B., Kass, D. A., Tomaselli, G. F., Kaab, S., Tunin, R. and Marban, E. (1999) Mechanisms of Altered Excitation-Contraction Coupling in Canine Tachycardia-Induced Heart Failure, I: Experimental Studies. *Circ Res* 84, 562-70.

Pitzalis, M. V., Iacoviello, M., Romito, R., Massari, F., Rizzon, B., Luzzi, G., Guida, P., Andriani, A., Mastropasqua, F. and Rizzon, P. (2002) Cardiac Resynchronization Therapy Tailored by Echocardiographic Evaluation of Ventricular Asynchrony. *J Am Coll Cardiol* 40, 1615-22.

Rice, J. J., Wang, F., Bers, D. M. and de Tombe, P. P. (2008) Approximate model of cooperative activation and crossbridge cycling in cardiac muscle using ordinary differential equations. *Biophys J* 95, 2368-90.

Russell, K., Smiseth, O. A., Gjesdal, O., Qvigstad, E., Norseng, P. A., Sjaastad, I., Opdahl, A., Skulstad, H., Edvardsen, T. and Remme, E. W. (2011) Mechanism of prolonged electromechanical delay in late activated myocardium during left bundle branch block. *Am J Physiol Heart Circ Physiol* 301, 112334-43.

Spragg, D. D., Dong, J., Fetics, B. J., Helm, R., Marine, J. E., Cheng, A., Henrikson, C. A., Kass, D. A. and Berger, R. D. (2010) Optimal left ventricular endocardial pacing sites for cardiac resynchronization therapy in patients with ischemic cardiomyopathy. *J Am Coll Cardiol* 56, 774-81.

St John Sutton, M. G., Plappert, T., Abraham, W. T., Smith, A. L., DeLurgio, D. B., Leon, A. R., Loh, E., Kocovic, D. Z., Fisher, W. G., Ellestad, M., Messenger, J., Kruger, K., Hilpisch, K. E. and Hill, M. R. (2003) Effect of Cardiac Resynchronization Therapy on Left Ventricular Size and Function in Chronic Heart Failure. *Circulation* 107, 1985-90.

Suffoletto, M. S., Dohi, K., Cannesson, M., Saba, S. and Gorcsan, J., 3rd. (2006) Novel speckle-tracking radial strain from routine black-and-white echocardiographic images to quantify dyssynchrony and predict response to cardiac resynchronization therapy. *Circulation* 113, 960-8.

Suga, H. (1990) Ventricular energetics. *Physiol Rev* 70, 247-77.

Sutton, M. G., Plappert, T., Hilpisch, K. E., Abraham, W. T., Hayes, D. L. and Chinchoy, E. (2006) Sustained Reverse Left Ventricular Structural Remodeling with Cardiac Resynchronization at One Year Is a Function of Etiology: Quantitative Doppler Echocardiographic Evidence from the Multicenter Insync Randomized Clinical Evaluation (MIRACLE). *Circulation* 113, 266-72.

Tyberg, J. V., Yeatman, L. A., Parmley, W. W., Urschel, C. W. and Sonnenblick, E. H. (1970) Effects of hypoxia on mechanics of cardiac contraction. *Am J Physiol* 218, 1780-8.

Ukkonen, H., Beanlands, R. S., Burwash, I. G., de Kemp, R. A., Nahmias, C., Fallen, E., Hill, M. R. and Tang, A. S. (2003) Effect of cardiac resynchronization on myocardial efficiency and regional oxidative metabolism. *Circulation* 107, 28-31.

Usyk, T. P. and McCulloch, A. D. (2003) Relationship between Regional Shortening and Asynchronous Electrical Activation in a Three-Dimensional Model of Ventricular Electromechanics. *J Cardiovasc Electrophysiol* 14, S196-202.

Vadakkumpadan, F., Arevalo, H., Prassl, A. J., Chen, J., Kickinger, F., Kohl, P., Plank, G. and Trayanova, N. (2010) Image-based models of cardiac structure in health and disease. *Wiley Interdiscip Rev Syst Biol Med* 2, 489-506.

van Deursen, C., van Geldorp, I. E., Rademakers, L. M., van Hunnik, A., Kuiper, M., Klersy, C., Auricchio, A. and Prinzen, F. W. (2009) Left ventricular endocardial pacing improves resynchronization therapy in canine left bundle-branch hearts. *Circ Arrhythm Electrophysiol* 2, 580-7.

Walker, J. C., Ratcliffe, M. B., Zhang, P., Wallace, A. W., Fata, B., Hsu, E. W., Saloner, D. and Guccione, J. M. (2005) MRI-based finite-element analysis of left ventricular aneurysm. *Am J Physiol Heart Circ Physiol* 289, H692-700.

White, J. A., Yee, R., Yuan, X., Krahn, A., Skanes, A., Parker, M., Klein, G. and Drangova, M. (2006) Delayed Enhancement Magnetic Resonance Imaging Predicts Response to Cardiac Resynchronization Therapy in Patients with Intraventricular Dyssynchrony. *J Am Coll Cardiol* 48, 1953-60.

Wu, Y., Bell, S. P., Trombitas, K., Witt, C. C., Labeit, S., LeWinter, M. M. and Granzier, H. (2002) Changes in Titin Isoform Expression in Pacing-Induced Cardiac Failure Give Rise to Increased Passive Muscle Stiffness. *Circulation* 106, 1384-9.

Yu, C. M., Chau, E., Sanderson, J. E., Fan, K., Tang, M. O., Fung, W. H., Lin, H., Kong, S. L., Lam, Y. M., Hill, M. R. and Lau, C. P. (2002) Tissue Doppler Echocardiographic Evidence of Reverse Remodeling and Improved Synchronicity by Simultaneously Delaying Regional Contraction after Biventricular Pacing Therapy in Heart Failure. *Circulation* 105, 438-45.

The above provides some examples according to particular embodiments of the current invention. The broad concepts of the current invention are not limited to only these particular examples. More generally, a method of planning a patient-specific cardiac procedure according to an embodiment of the current invention includes receiving three-dimensional imaging data of a patient's heart, simulating at least one of electrophysiological or electromechanical activity of at least a portion of the patient's heart using the three-dimensional imaging data, and planning the patient-specific cardiac procedure based on the simulating. The cardiac procedure is for providing a preselected alteration of at least one of electrophysiological or electromechanical behavior of the patient's heart.

The three-dimensional imaging data can be MRI data as described in the examples above. However, the broad concepts of the current invention are not limited to that particular example. The three-dimensional imaging data can be can be at least one of magnetic resonance imaging (MRI), computed tomography (CT), positron emission tomography (PET), ultrasound, or nuclear tracer three-dimensional imaging data, for example. The method of planning a patient-specific cardiac procedure can further include receiving additional patient-specific data in addition to the three-dimensional imaging data. For example, some embodiments can include receiving at least one of biopsy data, electrocardiogram data, recorded data from an implantable device (pace maker, defibrillator, etc.), or invasive electrical mapping data (e.g., endoscopic). The simulating can then use the additional patient-specific data for the simulation.

The simulating at least one of electrophysiological or electromechanical activity of at least the portion of the patient's heart can include constructing a geometric model of the portion of the patient's heart. The geometric model can include normal tissue regions and remodeled tissue regions that are determined for the patient using the three-dimensional imaging data. The term "remodeled tissue" can include infarct scar, infarct border (gray) zone, fibrosis, or other disease-related structural, electrophysiological or contractile changes in the heart. The simulating can further include estimating tissue fiber orientations in the geometric model of the portion of the patient's heart. The estimation of fiber orientations can be done in a variety of ways. For example, the fiber orientations can be calculated using a Laplace-Dirichlet method to define the local transmural and apicobasal axes at each spatial location in the ventricles, (J. D. Bayer, R. Blake, G. Plank, Trayanova N, Novel rule based algorithm for assigning myocardial fiber orientation to computation heart models. *Ann Biomed Eng.*, (in review) (2012), the entire contents of which are incorporated herein by reference). Another approach could utilize pre-compiled data (i.e., atlas data), which can be mapped onto the specific size and shape of the patient's heart (Image-Based Estimation of Ventricular Fiber Orientations for Personalized Modeling of Cardiac Electrophysiology, Vadakkumpadan F, Arevalo H, Ceritoglu C, Miller M, Trayanova N., IEEE Trans Med Imaging. 2012 Jan. 18. [Epub ahead of print], the entire contents of which are incorporated herein by reference).

A method of planning a patient-specific cardiac procedure according to an embodiment of the current invention can be directed to planning an ablation procedure to alleviate a ventricular arrhythmia. In this embodiment, the geometric model of the at least said portion of the patient's heart includes at least a geometric model of right and left ventricles of the patient's heart. The remodeled tissue regions in this case can be segmented into a plurality of different regions based on the three-dimensional imaging data. The plurality of different regions can include scar tissue regions, normal tissues regions, and transition zones, for example, between normal and scar tissue regions. The transition zones include infarct border zone tissue regions (we also refer to these zones as GZ, gray zones). The simulating in this case can be simulating electrophysiological activity of at least the right and left ventricles of the patient's heart. The ventricular arrhythmia can be ventricular tachycardia or ventricular fibrillation, for example. In an embodiment of the current invention, the planning of the patient-specific cardiac procedure includes identifying organizing centers of ventricular tachycardia from the simulation of electrophysiological activity. In some embodiments, the planning the patient-specific cardiac procedure can include identifying a critical pathway for ventricular tachycardia or three-dimensional scroll-wave filaments corresponding to the organizing centers as well as other slow conducting pathways through and around areas of scar tissue that are a part of a ventricular tachycardia circuit and further planning ablation to coincide with at least a portion of the three-dimensional scroll-wave filaments or other critical pathways for the ventricular tachycardia. (See above for some specific examples.)

In a method of planning a patient-specific cardiac procedure according to other embodiments of the current invention, the geometric model of the portion of the patient's heart includes a geometric model of at least right and left atria of the patient's heart. In this embodiment, the remodeled tissue regions are fibrotic tissue regions. The simulating at least one of electrophysiological or electromechanical activity is simulating electrophysiological activity of at least the right and left atria of the patient's heart. This embodiment is for planning an ablation procedure to alleviate atrial fibrillation.

In another embodiment, the simulating at least one of electrophysiological or electromechanical activity is simulating electromechanical activity of at least a portion of the patient's heart. The planning can include determining whether the patient is a suitable candidate for cardiac resynchronization therapy. If the patient is a suitable candidate for cardiac resynchronization therapy, further embodiments can include planning a location in which to attach at least one pacing lead for cardiac resynchronization therapy. Further embodiments can include, planning the location in which to attach at least one pacing lead for cardiac resynchronization therapy based on regions of longest electromechanical delay or regions of latest electrical or mechanical activation as determined from the simulation. Further embodiments can include, planning the location in which to attach at least one pacing lead for cardiac resynchronization therapy based on local or global energy consumption or myocardial efficiency, as determined from the simulation. Myocardial efficiency is the ratio of mechanical work performed by the ventricles to myocardial energy consumption.

The embodiments discussed in this specification are intended to explain concepts of the invention. However, the invention is not intended to be limited to the specific terminology selected and the particular examples described. The above-described embodiments of the invention may be modified or varied, without departing from the invention, as appreciated by those skilled in the art in light of the above teachings. It is therefore to be understood that, within the scope of the claims and their equivalents, the invention may be practiced otherwise than as specifically described.

We claim:

1. A non-invasive computer-implemented method of producing a personalized set of cardiac ablation targets to treat ventricular tachycardia in a living patient's heart, comprising:

receiving contrast-enhanced three-dimensional MRI or CT data of at least a portion of said living patient's heart;

segmenting said contrast-enhanced three-dimensional MRI or CT data to obtain three-dimensional heart image data;

segmenting said three-dimensional heart image data into at least three different tissue types of said heart based on said contrast-enhanced three-dimensional MRI or CT data, said at least three different tissue types including a normal tissue region, a scar tissue region and a transition zone region, said transition zone region including an infarct border zone tissue region and being characterized as having electrophysiological properties bounded by the properties of the normal and scar tissue regions;

constructing a model of at least a portion of said living patient's heart, said constructing said model comprising:

creating a finite element mesh using the segmented three-dimensional data, to provide a geometrical representation of said patient's heart, the finite element mesh comprising a plurality of volume elements, wherein the volume elements each represent a volume having an edge length in a range of about 300-400 microns;

determining a fiber orientation in each of the volume elements based on calculations executed on a patient-specific geometry of the patient's heart; and assigning electrophysiological parameters to each of the volume elements taking into account the determined fiber orientations and the type of tissue where the corresponding volume element is located;

simulating, using a computer, at least one of electrophysiological or electromechanical activity of at least a portion of said living patient's heart using said model, said simulating inducing an arrhythmia in said model of said living patient's heart;

producing, using said model, a personalized set of cardiac ablation targets representing locations in the heart critical to sustaining simulated ventricular tachycardia, such that when the targets are ablated, all simulated ventricular tachycardia is eliminated with a minimal ablation lesion size, wherein said producing a personalized set of cardiac ablation targets comprises simulating an initial target ablation, and upon the initial target ablation not eliminating all the simulated ventricular tachycardia re-calculating the personalized set of cardiac ablation targets; and exporting said personalized set of ablation targets for use during the ablation procedure to treat ventricular tachycardia.

2. The method of claim 1, further comprising:
receiving additional patient-specific data that includes at least one of biopsy data, electrocardiogram data, recorded data from an implantable device, or invasive electrical mapping data,
wherein said simulating uses said additional patient-specific data.

3. The method of claim 1, wherein said model of said at least said portion of said patient's heart includes at least a model of right and left ventricles of said patient's heart,
wherein said simulating at least one of electrophysiological or electromechanical activity is simulating electrophysiological activity of at least said right and left ventricles of said living patient's heart, and
wherein said producing said personalized set of ablation targets is providing a personalized set of cardiac ablation targets to alleviate a ventricular arrhythmia.

4. The method of claim 3, wherein said ventricular arrhythmia is a ventricular tachycardia.

5. The method of claim 3, wherein said producing said personalized set of cardiac ablation targets comprises identifying organizing centers of ventricular tachycardia from said simulating electrophysiological activity of at least said right and left ventricles of said living patient's heart.

6. The method of claim 5, wherein said producing said personalized set of cardiac ablation targets comprises identifying a critical pathway for ventricular tachycardia corresponding to said organizing centers as well as other slow conducting pathways through and around areas of scar tissue that are a part of a ventricular tachycardia circuit, and wherein said producing said personalized set of cardiac ablation targets further comprises providing said personalized set of cardiac ablation targets to coincide with at least a portion of said critical pathways for said ventricular tachycardia.

7. A non-transitory computer-readable medium comprising computer-executable code for producing a personalized set of cardiac ablation targets to treat ventricular tachycardia in a living patient's heart, said computer-executable code comprising instructions that, when executed by said computer, causes said computer to:

receive contrast-enhanced three-dimensional MRI or CT imaging data of at least a portion of said living patient's heart, said living patient's heart comprising normal tissue regions and remodeled tissue regions;

segment said contrast-enhanced three-dimensional MRI or CT data to obtain three-dimensional heart image data;

segment said three-dimensional heart image data into at least three different tissue types of said heart based on said contrast-enhanced three-dimensional MRI or CT data, said at least three different tissue types including a normal tissue region, a scar tissue region and a transition zone region, said transition zone region including an infarct border zone tissue region and being characterized as having electrophysiological properties bounded by the properties of the normal and scar tissue regions;

construct a model of at least a portion of said living patient's heart, said constructing said model comprising:

creating a finite element mesh using the segmented three-dimensional data, to provide a geometrical representation of said patient's heart, the finite element mesh comprising a plurality of volume elements, wherein the volume elements each represent a volume having an edge length in a range of about 300-400 microns;

determining a fiber orientation in each of the volume elements based on calculations executed on a patient-specific geometry of the patient's heart; and assigning electrophysiological parameters to each of the volume elements taking into account the determined fiber orientations and the type of tissue where the corresponding volume element is located;

simulate at least one of electrophysiological or electromechanical activity of at least a portion of said living patient's heart using said model, said simulating inducing an arrhythmia in said model of said living patient's heart;

produce, using said model, a personalized set of cardiac ablation targets representing locations in the heart critical to sustaining simulated ventricular tachycardia, such that when the targets are ablated, all simulated ventricular tachycardia is eliminated with a minimal ablation lesion size, wherein said producing a personalized set of cardiac ablation targets comprises simulating an initial target ablation, and upon the initial target ablation not eliminating all the simulated ventricular tachycardia re-calculating the personalized set of cardiac ablation targets; and export said personalized set of ablation targets for use in during the ablation procedure to treat ventricular tachycardia.

8. The computer-readable medium according to claim 7, said computer-executable code further comprising instructions that, when executed by said computer, causes said computer to:
receive additional patient-specific data that includes at least one of biopsy data, electrocardiogram data, recorded data from an implantable device, or invasive electrical mapping data,
wherein said simulation uses said additional patient-specific data.

9. The computer-readable medium according to claim 7, wherein said ventricular arrhythmia is a ventricular tachycardia.

10. The computer-readable medium according to claim 7, wherein said producing said personalized set of ablation targets comprises identifying organizing centers of ventricular tachycardia from said simulating electrophysiological activity of at least said right and left ventricles of said living patient's heart.

11. The computer-readable medium according to claim 7,
wherein said model of said at least said portion of said patient's heart includes at least a model of right and left atria of said living patient's heart,
wherein said remodeled tissue regions are fibrotic tissue regions,
wherein said simulating at least one of electrophysiological or electromechanical activity is simulating electrophysiological activity of at least said right and left atria of said living patient's heart, and
wherein said producing said personalized set of ablation targets includes providing an ablation target to alleviate atrial fibrillation.

12. A system for producing a personalized set of cardiac ablation targets to treat ventricular tachycardia in a living patient's heart comprising a data processor configured with computer-executable code, said computer-executable code comprising instructions that, when executed by said data processor, causes said data processor to:
receive contrast-enhanced magnetic resonance or CT three-dimensional imaging data of at least a portion of said living patient's heart, said patient's heart comprising normal tissue regions and remodeled tissue regions;
segment said contrast-enhanced magnetic resonance or CT three-dimensional imaging data to obtain three-dimensional heart image data;
segment said three-dimensional heart image data into at least three different tissue types of said heart based on said contrast-enhanced magnetic resonance or CT three-dimensional imaging data, said at least three different tissue types including a normal tissue region, a scar tissue region and a transition zone region, said transition zone region including an infarct border zone tissue region and being characterized as having electrophysiological properties bounded by the properties of the normal and scar tissue regions;
construct a model of at least a portion of said living patient's heart, said constructing said model comprising:
creating a finite element mesh using the segmented three-dimensional data, to provide a geometrical representation of said patient's heart, the finite element mesh comprising a plurality of volume elements, wherein the volume elements each represent a volume having an edge length in a range of about 300-400 microns;
determining a fiber orientation in each of the volume elements based on calculations executed on a patient-specific geometry of the patient's heart; and
assigning electrophysiological parameters to each of the volume elements taking into account the determined fiber orientations and the type of tissue where the corresponding volume element is located;
simulate at least one of electrophysiological or electromechanical activity of at least a portion of said living patient's heart using said model, said simulating inducing an arrhythmia in said model of said living patient's heart; and
produce, using said model, a personalized set of cardiac ablation targets representing locations in the heart critical to sustaining simulated ventricular tachycardia, such that when the targets are ablated, all simulated ventricular tachycardia is eliminated with a minimal ablation lesion size, wherein said producing a personalized set of cardiac ablation targets comprises simulating an initial target ablation, and upon the initial target ablation not eliminating all the simulated ventricular tachycardia re-calculating the personalized set of cardiac ablation targets; and
export said personalized set of ablation targets for use during the ablation procedure to treat ventricular tachycardia.

13. The system according to claim 12, said computer-executable code further comprising instructions that, when executed by said data processor, causes said data processor to:
receive additional patient-specific data that includes at least one of biopsy data, electrocardiogram data, recorded data from an implantable device, or invasive electrical mapping data,
wherein said simulation uses said additional patient-specific data.

14. The system according to claim 12, wherein said ventricular arrhythmia is a ventricular tachycardia.

15. The system according to claim 12, wherein said producing said personalized set of ablation targets comprises identifying organizing centers of ventricular tachycardia from said simulating electrophysiological activity of at least said right and left ventricles of said living patient's heart.

16. The system according to claim 12,
wherein said model of said at least said portion of said patient's heart includes at least a model of right and left atria of said patient's heart,
wherein said remodeled tissue regions are fibrotic tissue regions,
wherein said simulating at least one of electrophysiological or electromechanical activity is simulating electrophysiological activity of at least said right and left atria of said patient's heart, and
wherein said producing said personalized set of ablation targets includes providing an ablation target to alleviate atrial fibrillation.

17. The method of claim 1, further comprising segmenting said living patient's heart of said three-dimensional imaging data by demarcating epicardial and endocardial surfaces of said living patient's heart,
wherein said constructing said model is based on said segmenting.

18. The method of claim 1, wherein the determining fiber orientations comprises defining transmural and apicobasal directions of entire myocardium tissue of said living patient's heart.

19. The method of claim 18, wherein the determining fiber orientations comprises using bi-directional spherical linear interpolation to interpolate fiber orientations within the myocardium.

20. The method according to claim 1, further comprising:
generating a map of electrical activity of said living patient's heart registered to a geometrical representation of said living patient's heart,
wherein said producing said personalized set of ablation targets is based on said generating said map.

21. The computer-readable medium according to claim 7, wherein said instructions, when executed by said computer, further causes said computer to perform segmenting said living patient's heart of said three-dimensional imaging data by demarcating epicardial and endocardial surfaces of said living patient's heart,
wherein said constructing said model is based on said segmenting.

22. The computer-readable medium according to claim 7, wherein the determining fiber orientations comprises defining transmural and apicobasal directions of entire myocardium tissue of said living patient's heart.

23. The computer-readable medium according to claim 22, wherein the determining fiber orientations comprises using bi-directional spherical linear interpolation to interpolate fiber orientations within the myocardium.

24. The computer-readable medium according to claim 7, wherein said instructions, when executed by said computer, further causes said computer to perform:
generating a map of electrical activity of said living patient's heart registered to a geometrical representation of said living patient's heart,
wherein said producing said personalized set of ablation targets is based on said generating said map.

25. The system according to claim 12, wherein said computer-executable code further comprising instructions that, when executed by said data processor, causes said data processor to perform segmenting said living patient's heart of said three-dimensional imaging data by demarcating epicardial and endocardial surfaces of said living patient's heart,
wherein said constructing said model is based on said segmenting.

26. The system according to claim 12, wherein the determining fiber orientations comprises defining transmural and apicobasal directions of entire myocardium tissue of said living patient's heart.

27. The system according to claim 26, wherein the determining fiber orientations comprises using bi-directional spherical linear interpolation to interpolate fiber orientations within the myocardium.

28. The system according to claim 12, wherein said computer-executable code further comprising instructions that, when executed by said data processor, causes said data processor to perform generating a map of electrical activity of said living patient's heart registered to a geometrical representation of said living patient's heart,
wherein said producing said personalized set of ablation targets is based on said generating said map.

29. The method of claim 1, wherein the volume elements are tetrahedra-shaped.

30. The method of claim 1, further comprising:
stimulating left and right ventricles of the constructed model of the patient's heart to induce an arrhythmia,
wherein said simulating includes using said determined patient-specific ablation target at a plurality of locations in the left and right ventricles.

31. The computer-readable medium according to claim 7, wherein the volume elements are tetrahedra-shaped.

32. The computer-readable medium according to claim 7, wherein said computer-executable code further comprising instructions that, when executed by said computer, causes said computer to perform:
stimulating left and right ventricles of the constructed model of the patient's heart to induce an arrhythmia,
wherein said simulating includes using said determined personalized set of ablation targets at a plurality of locations in the left and right ventricles.

33. The system according to claim 12, wherein the volume elements are tetrahedra-shaped.

34. The system according to claim 12, wherein said computer-executable code further comprising instructions that, when executed by said data processor, causes said data processor to perform:
stimulating left and right ventricles of the constructed model of the patient's heart to induce an arrhythmia,
wherein said simulating includes using said determined personalized set of ablation targets at a plurality of locations in the left and right ventricles.

* * * * *